(12) United States Patent  (10) Patent No.: US 12,200,354 B2
Ozaki  (45) Date of Patent: Jan. 14, 2025

(54) INFORMATION PROCESSING APPARATUS AND TERMINAL DEVICE

(71) Applicant: SONY GROUP CORPORATION, Tokyo (JP)

(72) Inventor: Satoshi Ozaki, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 179 days.

(21) Appl. No.: 17/910,469

(22) PCT Filed: Feb. 16, 2021

(86) PCT No.: PCT/JP2021/005695
§ 371 (c)(1),
(2) Date: Sep. 9, 2022

(87) PCT Pub. No.: WO2021/186990
PCT Pub. Date: Sep. 23, 2021

(65) Prior Publication Data
US 2023/0033256 A1  Feb. 2, 2023

(30) Foreign Application Priority Data

Mar. 17, 2020 (JP) ................................. 2020-046749

(51) Int. Cl.
*H04N 23/00* (2023.01)
*H04M 1/02* (2006.01)
(Continued)

(52) U.S. Cl.
CPC .......... *H04N 23/64* (2023.01); *H04M 1/0266* (2013.01); *H04N 5/268* (2013.01);
(Continued)

(58) Field of Classification Search
CPC ...... H04N 23/64; H04N 5/268; H04N 23/611; H04N 23/632; H04N 23/90;
(Continued)

(56) References Cited

U.S. PATENT DOCUMENTS 4,398,811 A * 8/1983 Nishioka ............ G02B 23/2407
385/117
4,622,954 A * 11/1986 Arakawa .............. A61B 1/0051
600/153
(Continued)

FOREIGN PATENT DOCUMENTS

JP  2014-526312 A  10/2014
JP  2016-085322 A  5/2016
(Continued)

OTHER PUBLICATIONS

International Search Report and Written Opinion of PCT Application No. PCT/JP2021/005695, issued on May 18, 2021, 11 pages of ISRWO.

*Primary Examiner* — Frank F Huang
(74) *Attorney, Agent, or Firm* — CHIP LAW GROUP

(57) ABSTRACT

There is provided a device that causes a processor to execute detection of a first target in a first image acquired by a first camera, estimation of a length of a path from the detected first camera to the first target, and switching of display of a second image acquired by a second camera on the basis of the length of the path, and synthesis of an index for adjusting a position of a second target in the second image.

13 Claims, 18 Drawing Sheets

(51) Int. Cl.
  *H04N 5/268* (2006.01)
  *H04N 23/60* (2023.01)
  *H04N 23/611* (2023.01)
  *H04N 23/63* (2023.01)
  *H04N 23/90* (2023.01)
  *G06T 1/00* (2006.01)

(52) U.S. Cl.
  CPC ......... *H04N 23/611* (2023.01); *H04N 23/632* (2023.01); *H04N 23/90* (2023.01); *G06T 1/00* (2013.01); *H04M 2201/38* (2013.01); *H04M 2250/52* (2013.01)

(58) Field of Classification Search
  CPC ........... H04M 1/0266; H04M 2201/38; H04M 2250/52; G06T 1/00; A61B 3/0058; A61B 3/14
  See application file for complete search history.

(56) References Cited

U.S. PATENT DOCUMENTS

| | | | | |
|---|---|---|---|---|
| 4,905,082 | A * | 2/1990 | Nishigaki | A61B 1/07 600/109 |
| 5,557,454 | A * | 9/1996 | Takahashi | G02B 23/2415 348/45 |
| 6,025,873 | A * | 2/2000 | Nishioka | G02B 23/26 600/181 |
| 6,362,877 | B1 * | 3/2002 | Kobayashi | G01R 31/281 356/614 |
| 6,537,208 | B1 * | 3/2003 | Konno | H04N 5/2253 348/340 |
| 7,860,386 | B2 * | 12/2010 | Terashima | H04N 23/611 348/349 |
| 2002/0163742 | A1 * | 11/2002 | Togino | G02B 17/02 359/837 |
| 2003/0097044 | A1 * | 5/2003 | Rovegno | A61B 1/07 600/173 |
| 2005/0085698 | A1 * | 4/2005 | Bonningue | A61B 1/00183 600/129 |
| 2005/0197533 | A1 * | 9/2005 | May | A61B 1/042 600/137 |
| 2009/0292170 | A1 * | 11/2009 | Boebel | G02B 23/2415 600/111 |
| 2014/0071444 | A1 * | 3/2014 | Matsumoto | G01N 21/954 356/241.1 |
| 2014/0293043 | A1 * | 10/2014 | Datta | G06T 7/60 348/135 |
| 2016/0029896 | A1 | 2/2016 | Lee et al. | |
| 2016/0187652 | A1 | 6/2016 | Fujimaki | |
| 2016/0255324 | A1 * | 9/2016 | Kazakevich | G02B 23/2484 348/43 |
| 2016/0357007 | A1 * | 12/2016 | Swanson | G01B 9/02028 |
| 2018/0220952 | A1 | 8/2018 | Lee et al. | |
| 2018/0367786 | A1 * | 12/2018 | Furst | A61B 5/0073 |
| 2019/0028634 | A1 | 1/2019 | Koehler et al. | |
| 2023/0370046 | A1 * | 11/2023 | Kimura | H03H 9/02039 |

FOREIGN PATENT DOCUMENTS

| | | |
|---|---|---|
| JP | 6072798 B2 | 2/2017 |
| JP | 2019-506694 A | 3/2019 |
| WO | 2016/080031 A1 | 5/2016 |

* cited by examiner

INFORMATION PROCESSING APPARATUS AND TERMINAL DEVICE

CROSS REFERENCE TO RELATED APPLICATIONS

This application is a U.S. National Phase of International Patent Application No. PCT/JP2021/005695 filed on Feb. 16, 2021, which claims priority benefit of Japanese Patent Application No. JP 2020-046749 filed in the Japan Patent Office on Mar. 17, 2020. Each of the above-referenced applications is hereby incorporated herein by reference in its entirety.

TECHNICAL FIELD

The present disclosure relates to a program, an information processing apparatus, and a terminal device.

BACKGROUND ART

In ophthalmic diagnosis, it is desired that a patient takes an image of his/her eye using a terminal device such as a smartphone and the like and performs simple diagnosis at hand by processing such as AI and the like. For example, it is also conceivable that a determination is made as to whether or not it is necessary to go to a hospital by performing the simple diagnosis, or that a result of this simple diagnosis or the image is transmitted to a doctor, and the doctor remotely performs slightly more detailed diagnosis than the simple diagnosis from the diagnosis result, the image, and the like.

However, in order to acquire such an image, it is necessary to capture an image by bringing a lens attached to the terminal considerably close to the eye. For this reason, even if an in-camera capable of confirming a part of his/her face to be imaged at the time of imaging is used, it is difficult for the patient to see a screen of the smartphone. That is, it is difficult to confirm whether an image suitable for diagnosis can be captured at the timing of imaging. Furthermore, it is not limited to the eye, and it is also desired that the patient himself/herself appropriately capture images of facial skin, the inside of a mouth, and the like.

CITATION LIST

Patent Document

Patent Document 1: Japanese Patent Application Laid-Open No. 2014-526312

SUMMARY OF THE INVENTION

Problems to be Solved by the Invention

Therefore, the present disclosure realizes appropriate capturing of an image that cannot be directly viewed by a user.

Solutions to Problems

According to an embodiment, a program causes a processor to execute: detection of a first target in a first image acquired by a first camera; estimation of a length of a path from the detected first camera to the first target; and switching of display of a second image acquired by a second camera on the basis of the length of the path, and synthesis of an index for adjusting a position of a second target in the second image.

The first target may be a face of a user, and the second target may be an eye of the user.

The processor may process the first image and the second image acquired by a terminal device, the terminal device including a display, the first camera, and the second camera, the first camera being provided on the same surface as a display surface of the display, and the second camera being provided on a surface opposite to the display surface of the display.

Moreover, the processor may be caused to execute estimation of a region of the face reflected by a mirror acquired from the first camera, estimation of at least one of a distance from the mirror to the face or a distance from the mirror to the terminal device on the basis of the region of the face, and switching of the display of the second image between a case where the distance is shorter than a predetermined distance and a case where the distance is equal to or longer than the predetermined distance.

The processor may be caused to execute estimation of a distance from a terminal device including the second camera to a display existing outside the terminal device on the basis of the first image acquired by the first camera included in the display without reflection, and switching of the display of the second image between a case where the distance is shorter than a predetermined distance and a case where the distance is equal to or longer than the predetermined distance.

The processor may be caused to execute generation of the index such that at least a part of the eye falls within a predetermined range.

The processor may be caused to execute generation of the index such that at least a pupil of the eye falls within the predetermined range.

The processor may be caused to execute generation of the index such that at least an iris of the eye falls within the predetermined range.

The processor may be caused to execute analysis of the interior of the eye.

The processor may be caused to execute transmission of an image of the interior of the eye.

The processor may be caused to execute performance of authentication based on the iris.

The processor may be caused to execute displaying of the second image and the index on the display.

The first target may be a face of a user, and the second target may be facial skin of the user or an oral cavity of the user.

According to an embodiment, an information processing apparatus includes: a processor, in which the processor estimates a distance from a display to a user on the basis of a first image of the user and a terminal device captured by a first camera that captures an image in the same direction as a display surface of the display, and switches a second image captured by a second camera included in the terminal device on the basis of the distance, and outputs an image synthesized with an index to the display.

According to an embodiment, a terminal device includes: a display; a first camera that captures an image in the same direction as a display surface of the display; a second camera that captures an image in a direction opposite to the display surface of the display; and a processor, in which the processor estimates either one of a distance from a mirror to a face of a user and a distance from the mirror to the terminal device on the basis of a first image captured by the first camera of the face and the terminal device reflected by the mirror, and switches a second image captured by the second camera on the basis of the distance, and outputs an image synthesized with an index to the display.

By the program described above or a program that causes the processor of the information processing apparatus described above or the terminal device described above to execute processing, the processor may determine whether the second camera is at an appropriate position on the basis of the index, and generate the index based on a determination result.

By the program described above or a program that causes the processor of the information processing apparatus described above or the terminal device described above to execute processing, the processor may assign information including mirror writing to the index.

By the program described above or a program that causes the processor of the information processing apparatus described above or the terminal device described above to execute processing, the processor may assign color information to the index.

By the program described above or a program that causes the processor of the information processing apparatus described above or the terminal device described above to execute processing, the processor may determine whether the second camera is at an appropriate position on the basis of the index, and output sound on the basis of a determination result.

By the program described above or a program that causes the processor of the information processing apparatus described above or the terminal device described above to execute processing, the processor may determine whether the second camera is at an appropriate position on the basis of the index, and output vibration on the basis of a determination result.

By the program described above or a program that causes the processor of the information processing apparatus described above or the terminal device described above to execute processing, the processor may estimate the distance on the basis of an output from a TOF sensor.

By the program described above or a program that causes the processor of the information processing apparatus described above or the terminal device described above to execute processing, the processor may estimate the distance on the basis of a communication state between the terminal device and the display.

By the program described above or a program that causes the processor of the information processing apparatus described above or the terminal device described above to execute processing, the processor may switch the second image on the basis of eyesight of the user.

According to an embodiment, a server includes a second processor that performs at least part of processing in the processor described above.

According to an embodiment, a non-transitory computer readable medium records a program for causing the processor described above to execute processing.

MODES FOR CARRYING OUT THE INVENTION

Hereinafter, embodiments of the present disclosure will be described with reference to the drawings. In the description, a smartphone is used, but is not limited thereto, and a portable terminal having an in-camera and an out-camera, for example, a feature phone, a tablet terminal, and the like can similarly perform processing.

In the present disclosure, "camera" is a device in a broad sense having a function of collecting an electromagnetic wave having a predetermined wavelength, sensing the collected electromagnetic wave, and converting the collected electromagnetic wave into an electric signal, and is not limited to a camera and the like mounted on a general smartphone and the like. Here, the predetermined wavelength may be expressed, for example, in a range such as visible light or infrared light. Furthermore, the camera used for distance measurement may be, for example, a device that estimates a position of a target by reflection of a sound wave or an ultrasonic wave.

In the present disclosure, "direction of surface" is a normal direction of a surface. For example, a direction of a display surface of a display indicates a direction perpendicular to the display surface of the display. More specifically, it may be an imaging direction of a camera (in-camera) provided on a display side of the smartphone.

Figure 1:
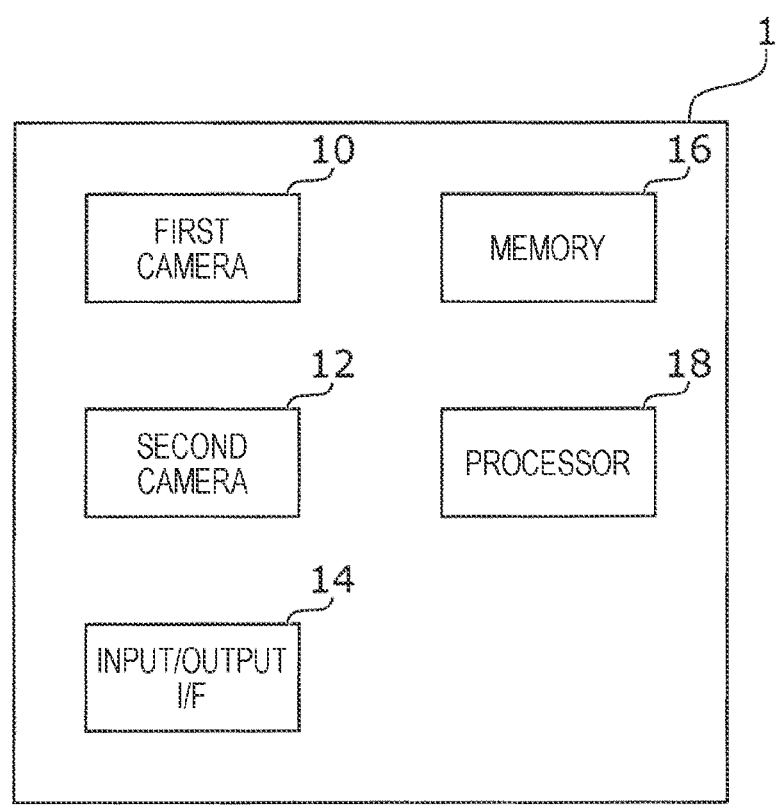
FIG. 1 is a diagram schematically illustrating a terminal device according to an embodiment.

FIG. 1 is a block diagram showing a configuration of a terminal device according to an embodiment. A terminal device 1 includes a first camera 10, a second camera 12, an input/output I/F 14, a memory 16, and a processor 18. The terminal device 1 is, for example, a smartphone, and in a case of the smartphone, the terminal device includes a touch screen as the input/output I/F 14, and includes the first camera 10 on the same surface as the touch screen and the second camera 12 on an opposite surface. Note that the terminal device 1 is not limited to having only this configuration, and a configuration for exerting functions of the terminal device 1 is provided in addition to this configuration.

The first camera 10 is, for example, a so-called in-camera, and captures an image in the same direction as a direction of the display (touch screen). The first camera 10 is used, for example, to image a user himself/herself and a rear side of the user from the terminal device 1 while the display is viewed.

The second camera 12 is, for example, a so-called out-camera, is provided on a surface opposite to the display, and captures an image in a direction opposite to the display. Note that, in a terminal device having displays on both sides, for example, the first camera 10 may be provided on a main display side, and the second camera 12 may be provided on a sub display side.

In general, the second camera 12 is often higher in performance, for example, higher in resolution and sensitivity than the first camera 10 provided on the display side. For this reason, it is desirable that the second camera 12 images information for which details are desired to be known. For example, in a case where an image of an eye is acquired and some sort of determination is made on appearance and the inside of the eye, it is desirable to acquire the image of the eye by the second camera 12.

The input/output I/F 14 is an interface for inputting/outputting information between the terminal device 1 and the outside. The input/output I/F 14 includes, for example, a display, a touch panel, a communication I/F, a microphone, a speaker, a physical switch, and the like. Furthermore, in a case where the terminal device 1 is a PC and the like, a keyboard, a mouse, and the like may be included. In a case where the terminal device 1 is a smartphone, for example, an image is output from a touch screen and an input from a user is received.

The memory 16 stores data used for information processing in the terminal device 1. This memory 16 may include, for example, a nonvolatile or volatile storage, and this type is not limited. Furthermore, the memory may be a memory that simply stores data such as a photograph, a voice, a document, and the like.

The processor 18 executes information processing in the terminal device 1. This processor 18 may include, for example, an accelerator such as a graphics processing unit (GPU) and the like in addition to a central processing unit (CPU). For example, the information processing according to the present embodiment is specifically executed by hardware by this processor 18 executing a program stored in the memory 16. Furthermore, the processor 18 also controls imaging of the camera, display of the display, and the like.

Figure 2:
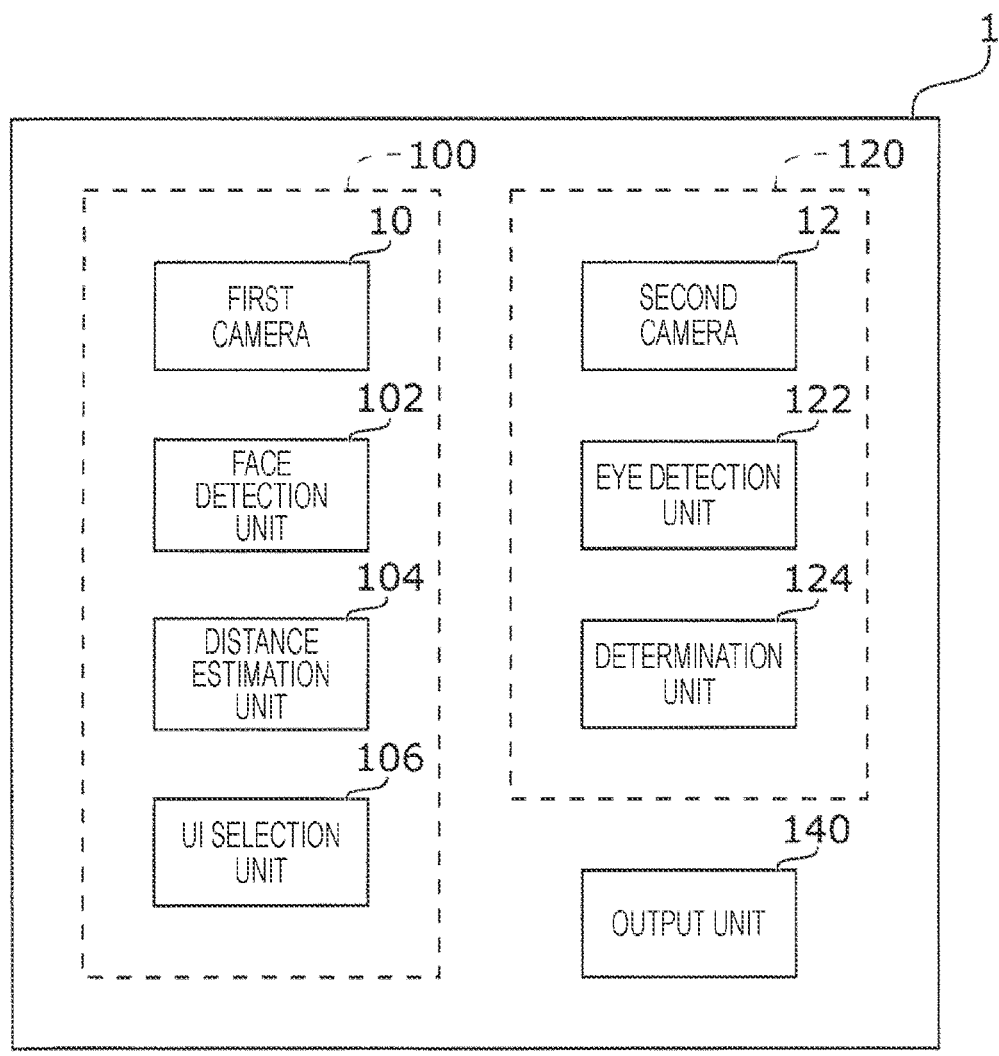
FIG. 2 is a diagram illustrating functions of the terminal device according to the embodiment.

FIG. 2 is a diagram illustrating a part of functions implemented by the processor 18 of the terminal device 1 according to the present embodiment. Hereinafter, the description will be given using a smartphone, but the present embodiment is not limited thereto, and can also be applied to a device in which cameras are provided on a front surface and a back surface and one of the cameras is provided on a display side, for example, a tablet terminal or a feature phone. Furthermore, modes different from these will be described later.

The terminal device 1 can realize processing by a first processing unit 100 and a second processing unit 120. These processing units are implemented, for example, by the processor 18.

The first processing unit 100 includes the first camera 10, a face detection unit 102, a distance estimation unit 104, and a UI selection unit 106. The first processing unit 100 executes processing based on information acquired by the first camera 10. The first camera 10 has the function as described above.

Figure 3:
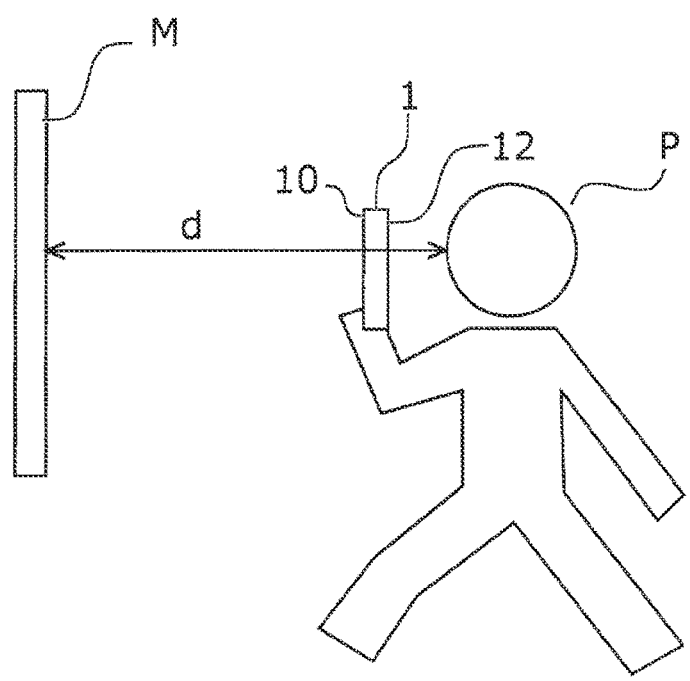
FIG. 3 is a diagram schematically illustrating a usage example of the terminal device according to the embodiment.

FIG. 3 is a diagram schematically illustrating use of the terminal device 1 when executing information processing according to the embodiment. A user P holds the terminal device 1 in front of a face, for example, between him/her and a mirror M such that the second camera 12 captures an eye. Then, the user P checks a display reflected by the mirror M to adjust a position of an image to be captured.

Figure 4:
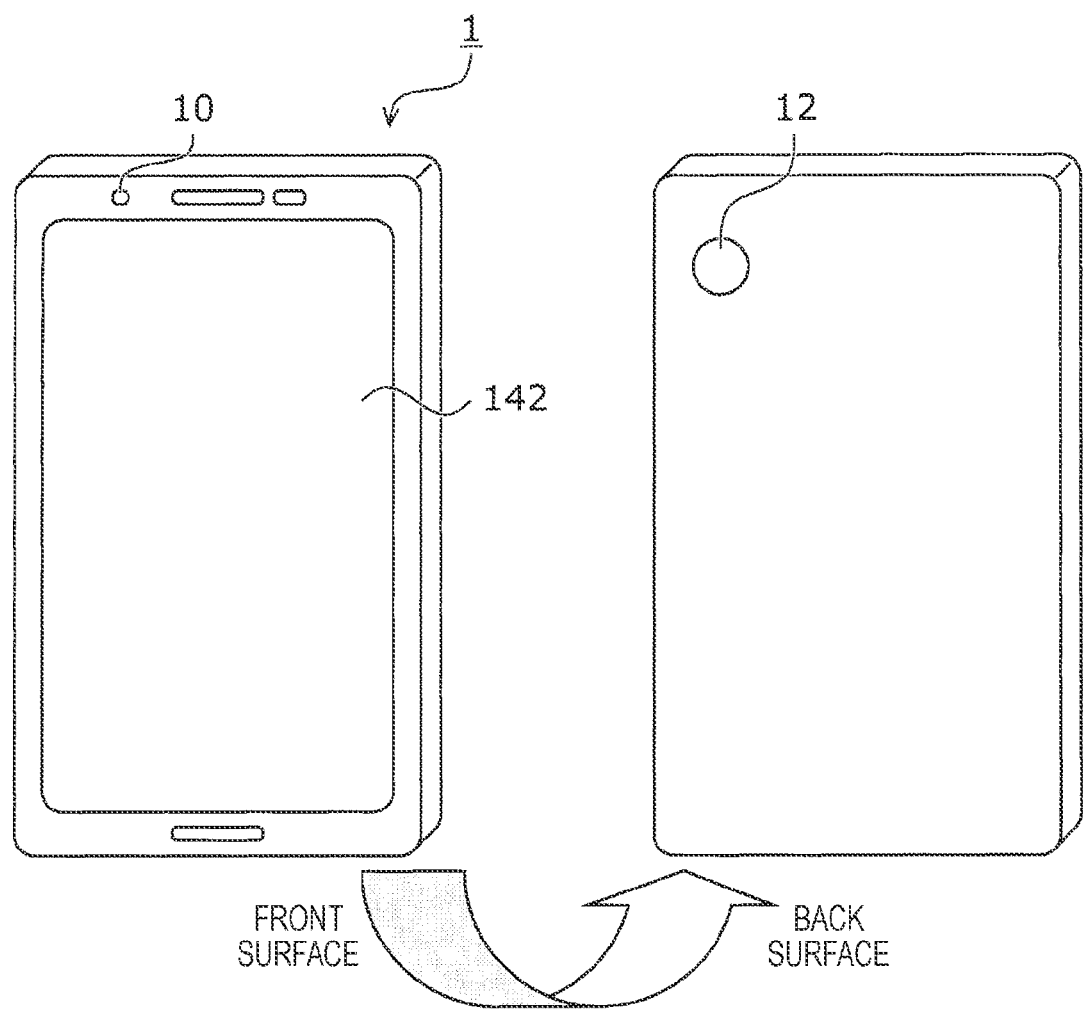
FIG. 4 is a diagram illustrating an example of the terminal device according to the embodiment.

FIG. 4 is a diagram illustrating an example of the terminal device 1 according to the embodiment. As illustrated in this drawing, the terminal device 1 includes a display 142 as a part of an output unit 140. The display 142 is, for example, a touch screen. The first camera 10 is provided on a front surface that is the same surface as the display 142, and the second camera 12 is provided on a back surface. Furthermore, the display 142 and the first camera 10 are explicitly illustrated in FIG. 4, but not limited thereto, and for example, the first camera 10 may be arranged to overlap the display 142. Note that the front surface and the back surface are relatively determined, and the names are not limited thereto.

The first processing unit 100 executes processing of selecting a UI of a second image to be output to the display 142 on the basis of a distance between the user P and the mirror M using the first camera in arrangement in FIG. 4. For example, the UI is switched by selecting a short distance UI in a case where a distance d is less than a predetermined distance, and selecting a long distance UI in a case where the distance d is equal to or greater than the predetermined distance. The predetermined distance may be a value having a width satisfying a first predetermined distance<a second predetermined distance. In this case, the long distance UI may be selected as an initial state, and switching to the short distance UI may be selected in a case where the distance d<the first predetermined distance, and switching to the long distance UI may be selected in a case where the second predetermined distance<the distance d.

Note that, in the present disclosure, it is assumed that equal to or less than, equal to or greater than, less than, and greater than are used flexibly, and a combination of equal to or less than and greater than and that of less than and equal to or greater than may be interchanged, and the same applies to an inequality sign.

The face detection unit 102 in FIG. 2 detects a face region of the user P from the information acquired by the first camera 10. For example, the first camera 10 acquires information of the mirror M reflecting the user P as a first image. This image may be a still image or a moving image.

The distance estimation unit 104 estimates the distance d between the user P and the mirror M on the basis of a detection result of a region of the face (first target) of the user P detected by the face detection unit 102. Note that this distance may be a distance between the terminal device 1 (or the first camera 10) and the mirror M instead of the user P and the mirror M.

The UI selection unit 106 selects a user interface (UI) to be displayed on the display on the basis of the distance d estimated by the distance estimation unit 104.

The second processing unit 120 includes the second camera 12, an eye detection unit 122, and a determination unit 124. This second processing unit 120 executes processing based on information acquired by the second camera 12. The second camera 12 has the function as described above.

The eye detection unit 122 detects a position of the eye (second target) of the user P from the information acquired by the second camera 12. For example, the eye detection unit 122 detects a position of a pupil of the eye of the user P or a position of an iris of the eye of the user P. For example, the second camera 12 acquires information of a part of the face of the user P as the second image. This image may be a still image or a moving image.

After the second camera 12 acquires the second image including the information of the eye detected by the eye detection unit 122, the determination unit 124 performs determination on the basis of the second image. This determination is, for example, a determination that it is better to receive an inspection because an abnormality is recognized, or that no abnormality is particularly recognized.

The output unit 140 outputs a result determined by the determination unit 124.

Furthermore, the output unit 140 may perform output via the display 142. By outputting the second image to the display 142, the second image is output to the user P via the mirror M. This output second image is generated on the basis of the UI selected by the UI selection unit 106.

Figure 5:
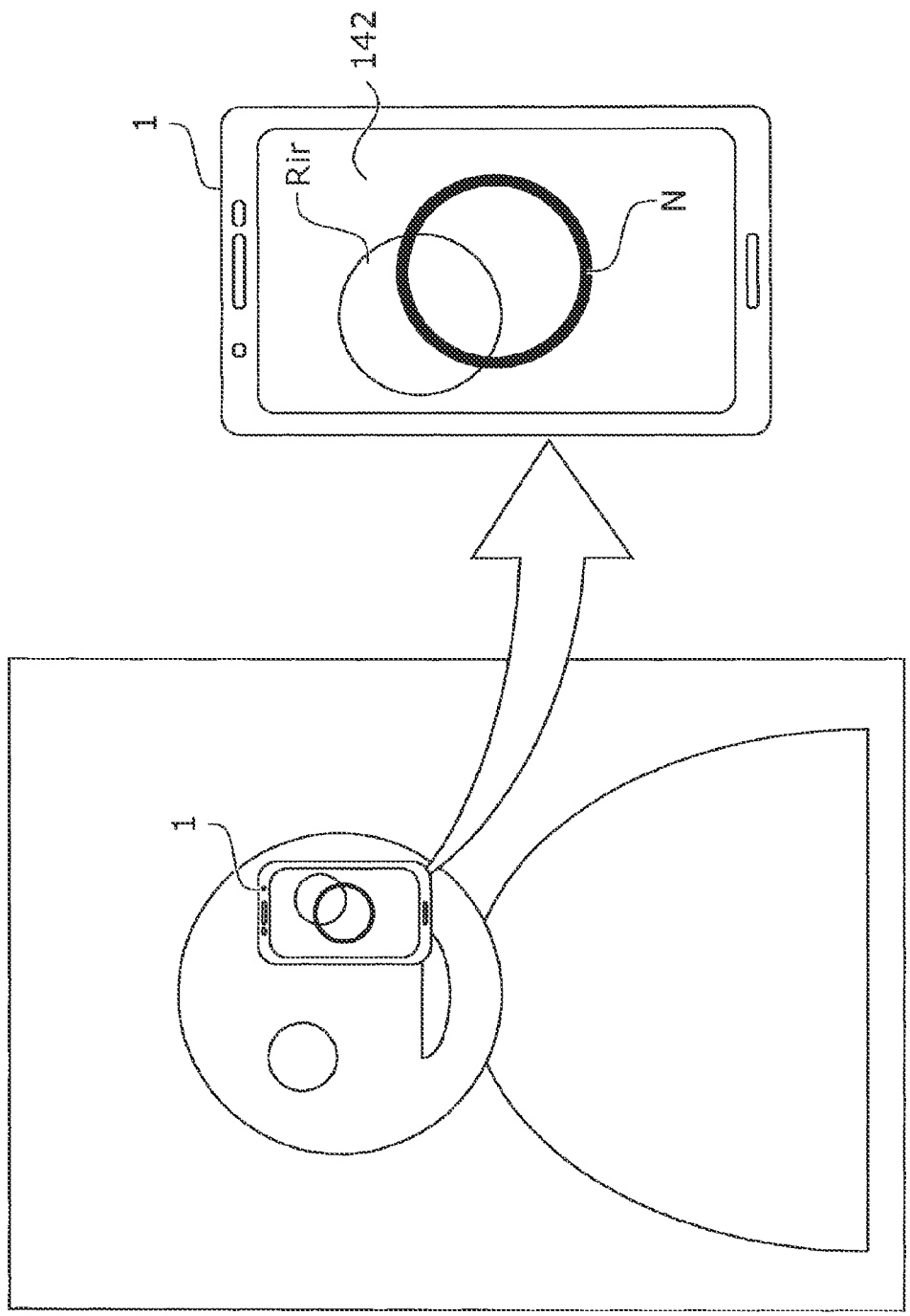
FIG. 5 is a diagram illustrating a display example of a display according to the embodiment.

FIG. 5 is a diagram illustrating an example of the second image in a case where the long distance UI to be output to the display 142 is selected. The terminal device 1 activates, for example, an application for determining an image of an eye to bring the terminal device into a state capable of executing the functions described above. This second image displayed on the display 142 is obtained by applying the long distance UI onto the application. A diagram illustrated on the right is a diagram illustrating the display 142 of the terminal device 1. In a left drawing, the left and right of the terminal device 1 are reversed because of reflection by the mirror M.

As illustrated in the drawing, an index (hereinafter referred to as navigation N) and a region Rir of an iris are displayed on the display 142. The navigation N is set in the output unit 140 and is an index for instructing the user P to set the iris in this range. That is, the terminal device 1 first generates the navigation N using the application, and synthesizes the navigation N with the second image according to each distance.

The region Rir of the iris is obtained by extracting and displaying the region of the iris of the user P in the image acquired by the second camera 12. This may be a region of the pupil. In the long distance UI, for example, this region is filled with a predetermined color different from the color of the navigation N and displayed. In the long distance UI, in a case where the user P is away from the mirror M to some extent (farther than the predetermined distance), the second image synthesized with the navigation N by deformation is output to the display 142. In this way, in a case where the user P is away from the mirror M, it is possible to adjust a position of the eye, that is, adjust a position of the terminal device 1 with respect to the face of the user P as an easy-to-understand display.

The region Rir of the iris is shown as being circular, but may, for example, represent a missing part due to an eyelid in a case where the eyelid overlaps the iris. However, even in a case where a part of the iris is missing in the image, the region Rir of the iris may be estimated and indicated as a circle.

Furthermore, the region of the pupil may be adjusted to acquire an image of the pupil instead of the iris.

Figure 6:
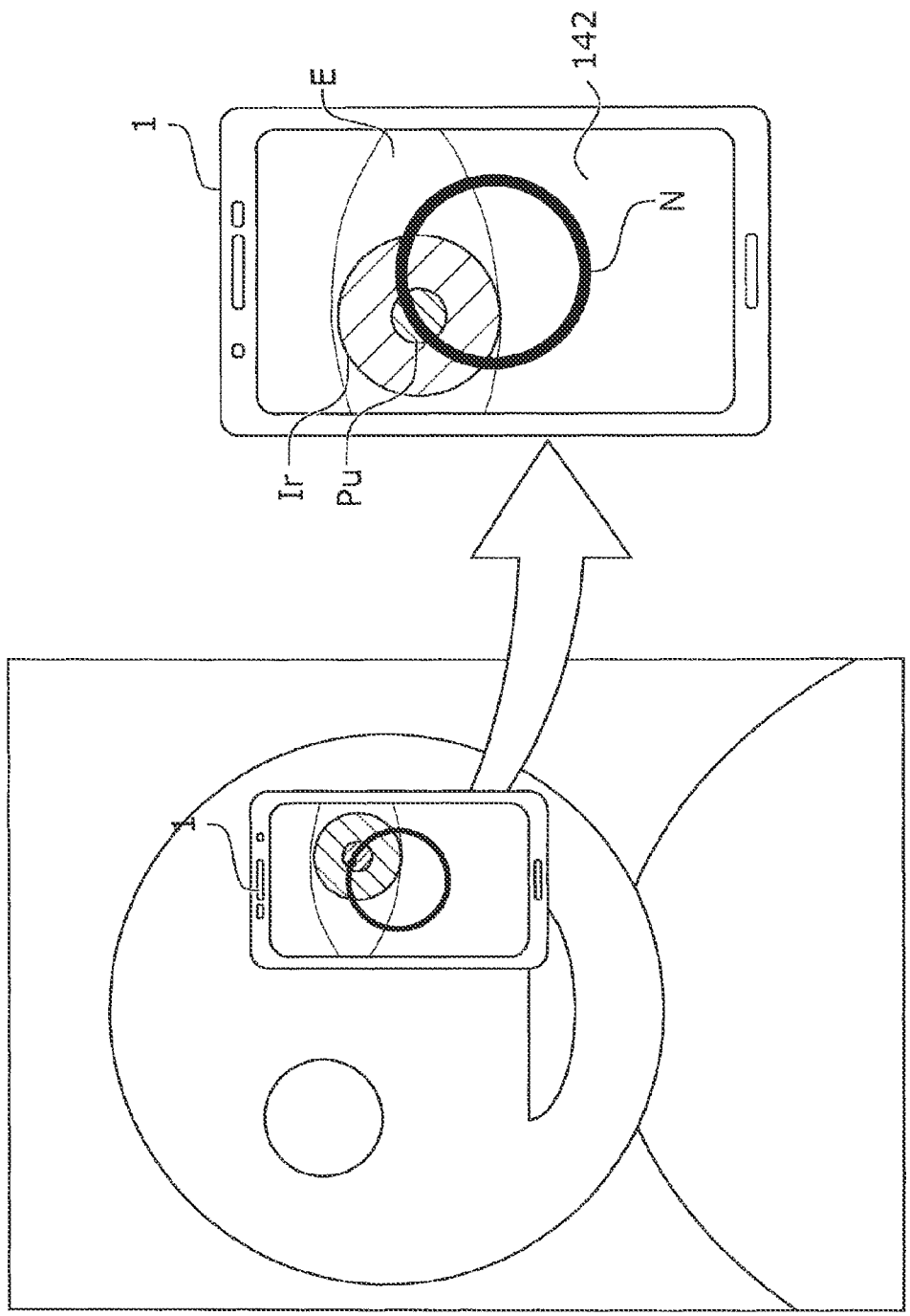
FIG. 6 is a diagram illustrating a display example of the display according to the embodiment.

FIG. 6 is a diagram illustrating an example of the second image in a case where the short distance UI to be output to the display 142 is selected. This second image displayed on the display 142 is obtained by applying the short distance UI. A diagram illustrated on the right is an enlarged view of the terminal device 1.

As illustrated in the drawing, the navigation N, an iris Ir, and a pupil Pu are displayed on the display 142. Similarly to the above, the user P adjusts the position of the terminal device 1 so that the iris Ir fits in the navigation N. Similarly to the above, the position of the pupil Pu may be adjusted instead of the iris Ir.

Unlike FIG. 5, a more detailed eye state is output as the second image. In the short distance UI, for example, the information acquired by the second camera 12 may be displayed without being particularly deformed. By displaying in this manner, the user P can more accurately adjust an imaging position.

Figure 7:
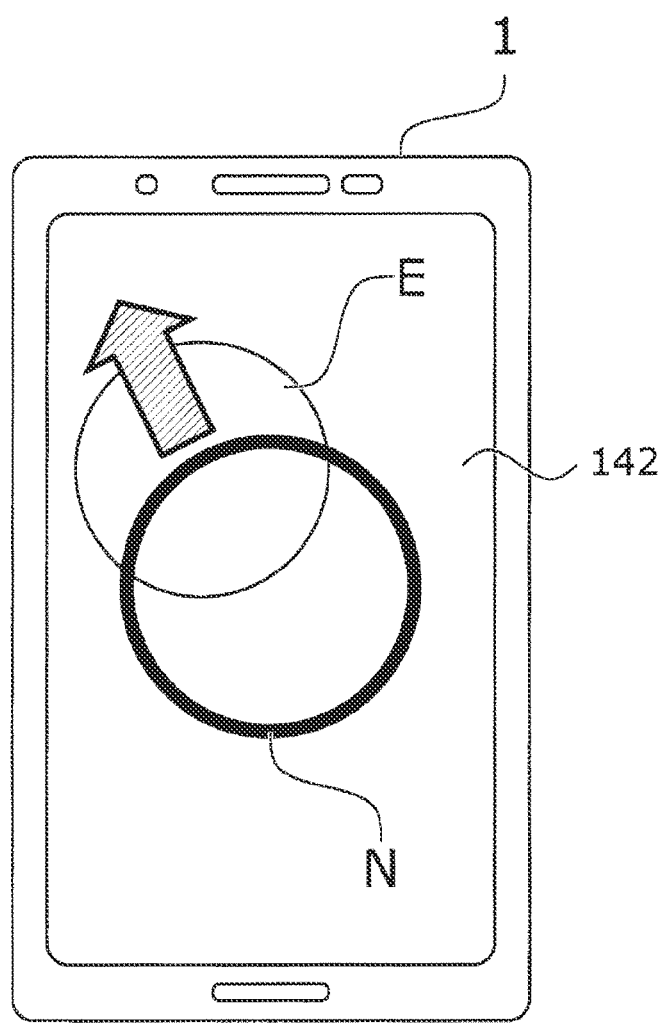
FIG. 7 is a diagram illustrating a display example of the display according to the embodiment.

FIG. 7 is a diagram illustrating an example of the navigation N in the embodiment. For example, the second image using the long distance UI is output to the display 142.

In a case where an eye E is not aligned with the navigation N, an indicator may be displayed for alignment. For example, this indicator is indicated by an arrow as shown in the drawing. The user P can perform alignment by shifting the terminal device 1 in a direction of the arrow in the second image captured in the mirror M.

The indicator is not limited to the arrow, and may be represented by, for example, a simpler triangle. Furthermore, a large arrow may be displayed in a light color and the like so as to use the entire display 142. Furthermore, the display may be changed so that a longer arrow, a darker arrow, and the like are used as a distance for adjusting the position is longer.

Furthermore, color of the navigation N may be changed between a case where the position adjustment is shifted and a case where the position adjustment is successful. For example, although initially indicated by a red circle, the color may change in a gradation manner so as to become green as accuracy of the position adjustment increases.

Furthermore, it is not limited to the display, and for example, the output unit 140 may control stereo and the like so that a larger sound is emitted as the position is farther away. As another example, the output unit 140 may control a vibrator such that vibration becomes larger as the position is farther away.

During a series of work performed by the user P, a finger may touch the display 142. In such a case, special processing, for example, processing of responding to a tap, a swipe, and the like may be controlled so as not to minimize, stop, and the like the application.

Figure 8:
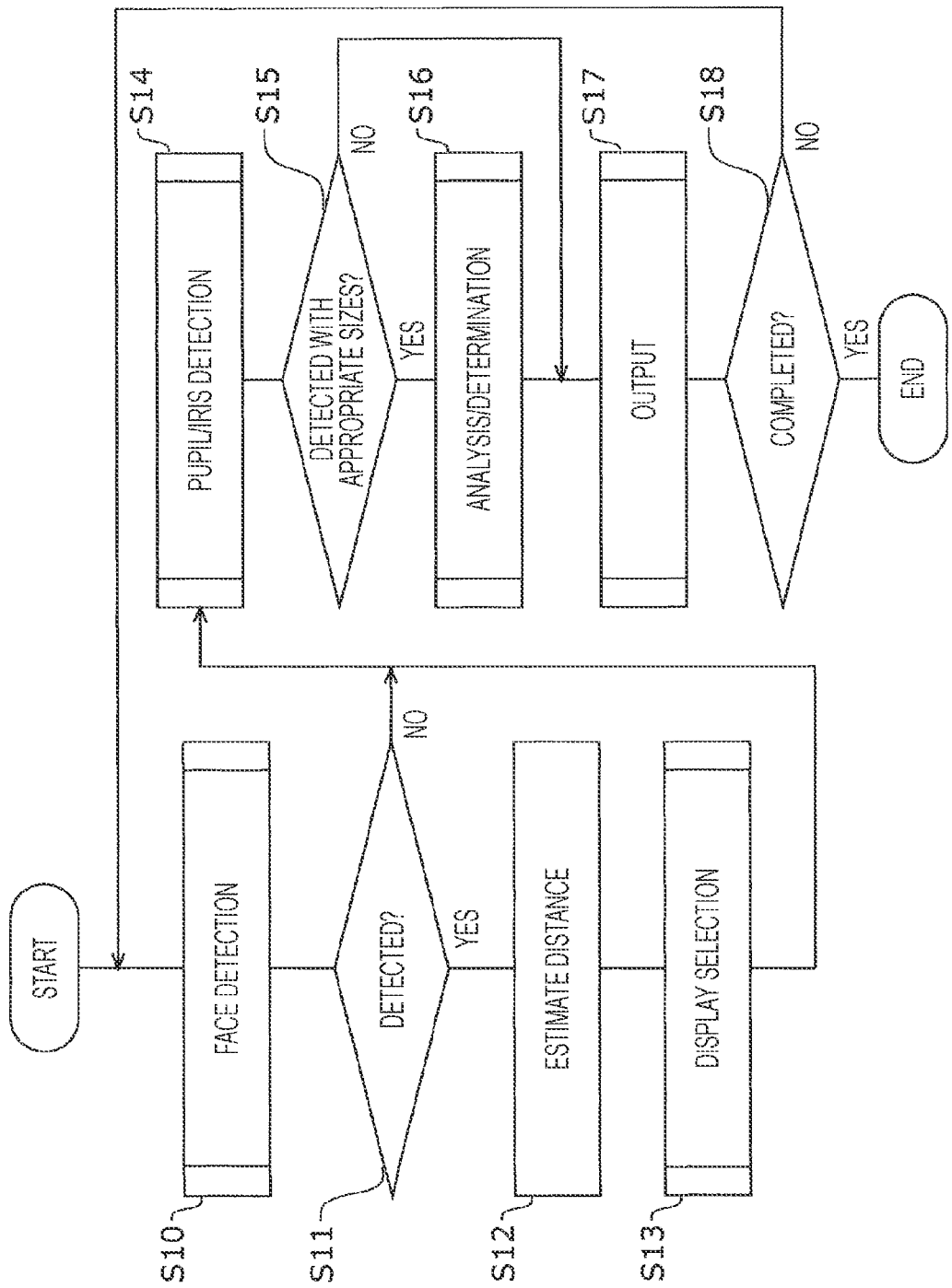
FIG. 8 is a flowchart illustrating processing according to the embodiment.

FIG. 8 is a flowchart summarizing the processing described above according to the embodiment. The processing will be described with reference to this flowchart.

First, the face detection unit 102 acquires an image of the user P reflected by the mirror M using the first camera 10, and detects a face of the user P from the image (S10).

Figure 9:
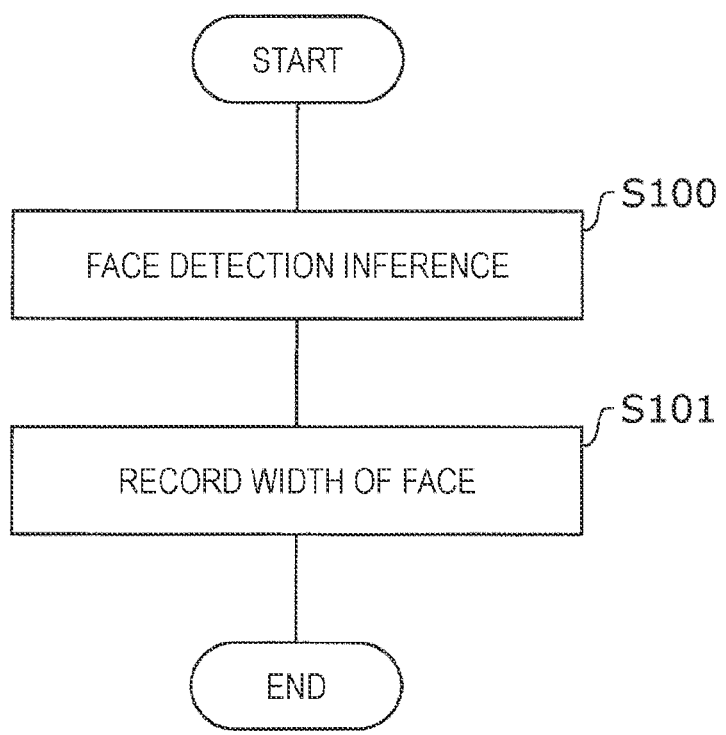
FIG. 9 is a flowchart illustrating processing according to the embodiment.

FIG. 9 is a flowchart illustrating a subroutine of this face detection (S10). The face detection unit 102 executes face detection inference using, for example, a learned neural network model (S100). This neural network is desirably optimized as a model capable of detecting a human face even if a part of the face is hidden, for example.

This model is optimized by performing machine learning in advance using, for example, a large amount of data each with a rectangular label of an image including a face and a face position as training data. Parameters of the optimized model are stored in, for example, the memory 16, and the face detection unit 102 forms a model and realizes inference by loading hyperparameters and parameters related to this model. For example, a detection result may be indicated by a rectangle, or may be a region of a face that can be extracted by a curve. The training data may include, for example, masking data. In this case, probability of detecting a face can be improved even in a state of wearing a mask.

Next, the face detection unit 102 records width of a face in the detected face (S101). The recording is executed, for example, by storing data in the memory 16. The width of the face is recorded, for example, in units of pixels. For example, in a case where the region of the face is obtained by a rectangle, the face detection unit 102 acquires the number of pixels in a horizontal direction of the rectangle region, and in a case where the region of the face is extracted by a curve, the face detection unit acquires the largest number of pixels in the horizontal direction.

Note that the face detection unit 102 may detect a plurality of faces in the first image, for example, in a case where there has been a plurality of persons in front of the mirror M and the like. In this case, a position of a person having the maximum width of the face described above may be determined as the position of the user P, and this width may be stored in the memory 16.

The face detection unit 102 executes face detection inference by the processing described above. In a case where the face has not been able to be detected, the failure is recorded. This recording may be performed, for example, by setting a flag as a temporary variable.

Next, the processor 18 determines whether or not the face has been able to be detected (S11).

In a case where the face has been able to be detected (S11: YES), the distance estimation unit 104 estimates a distance between the user P and the mirror M (S12). This distance estimation is executed on the basis of an estimated value of the width of the face acquired in step S10 and a specification of the first camera 10.

Figure 10:
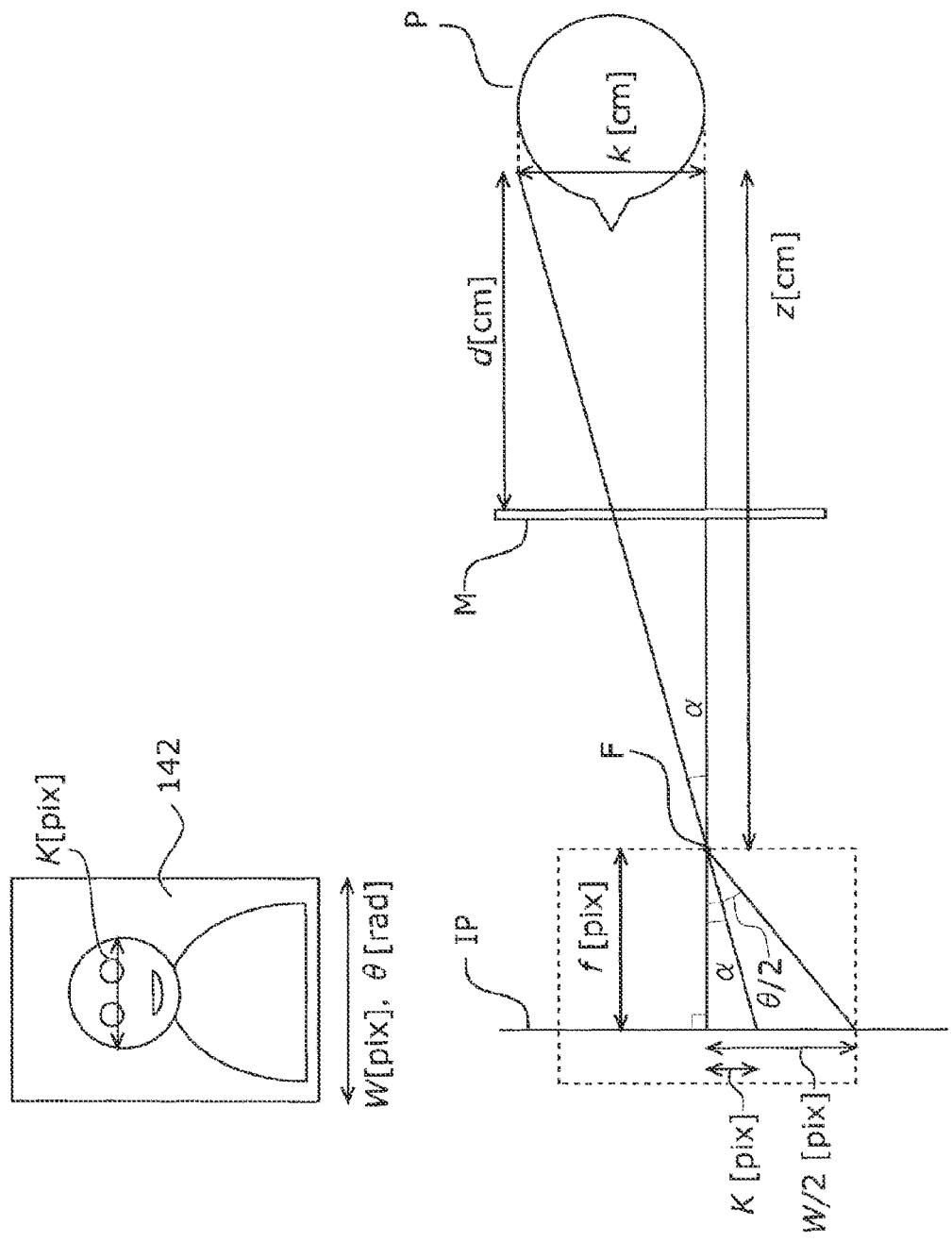
FIG. 10 is a diagram illustrating information about distance estimation according to the embodiment.

In FIG. 10, an upper diagram illustrates the first image displayed on the display 142, and a lower diagram is a plan view seen from above of the state of FIG. 3 in a case where the first image is captured.

In the first image, width of the face of the user P is assumed to be K pixels. Then, it is assumed that the number of pixels of the entire first image acquired from the specification of the first camera 10 is W pixels and an angle of view thereof is θ radians. A dotted line in the lower diagram indicates positions of an optical system and an image surface in a case where the first camera 10 is assumed to be a pinhole camera. Since an in-camera mounted on a smartphone and the like increases depth of field, an error in units of several mm occurs by making such an assumption, but this does not cause a big problem in a method of the present disclosure. Furthermore, in the position of the face of the user P, a line connecting an end of the face (an end of the face of a mirror image because of being actually reflected in the mirror) and an end of the face in the image surface is parallel to an optical axis, but this is for ease of calculation and does not affect a result. Note that although this drawing is drawn to be shifted in scale for the sake of explanation, f and W are actually smaller in ratio than the drawing.

When K and W are reflected in the lower diagram, as illustrated in the drawing, size is in units of pixels on the image surface. A focal length of the first camera 10 is represented by f pixels. Then, the following formula is established by a similarity relation between triangles.

[Mathematical formula 1]

$$\frac{K}{f} = \frac{k}{z} \quad (1)$$

Here, z is a distance twice as long as the distance d between the user P and the mirror M, and k is size of the actual width of the face of the user P.

Furthermore, the focal length f can be expressed as follows using the angle of view θ and W.

[Mathematical formula 2]

$$f = \frac{\frac{W}{2}}{\tan\frac{\theta}{2}} \quad (2)$$

When the formula (2) is substituted into the formula (1), the following formula is obtained.

[Mathematical formula 3]

$$z = \frac{k \cdot \frac{W}{2}}{K \cdot \tan\frac{\theta}{2}} \quad (3)$$

θ and W are known from the specification of the first camera 10, and K can be acquired from the first image. Therefore, if a value of k is known, z can be obtained. For example, z can be obtained by assuming that the width of the human face is 20 cm and the like. This assumption of k also has a small influence on the present disclosure. This k may be another value depending on, for example, age, sex, race, and the like. Furthermore, the user P may input this value of k.

On the basis of the formulas described above and the value of k, the processor 18 calculates the value of z, and then, a value of the distance d between the user P and the mirror M (S12). Note that the values unique to the first camera 10 may be determined, for example, on the basis of a database and the like in which values related to various terminal devices 1 are recorded at the time of installing an application in the terminal device 1. For example, in a case of a smartphone, values extracted from a specification of the smartphone may be stored, and an installer may determine a model of the terminal device 1 at the time of installation and acquire these values. Furthermore, measurement may be performed in some form such as using a test chart and the like, and a value thereof may be set.

Returning to FIG. 8, continuation of the processing will be described.

Next, the UI selection unit 106 selects whether to use the short distance UI or the long distance UI for display (S13).

Figure 11:
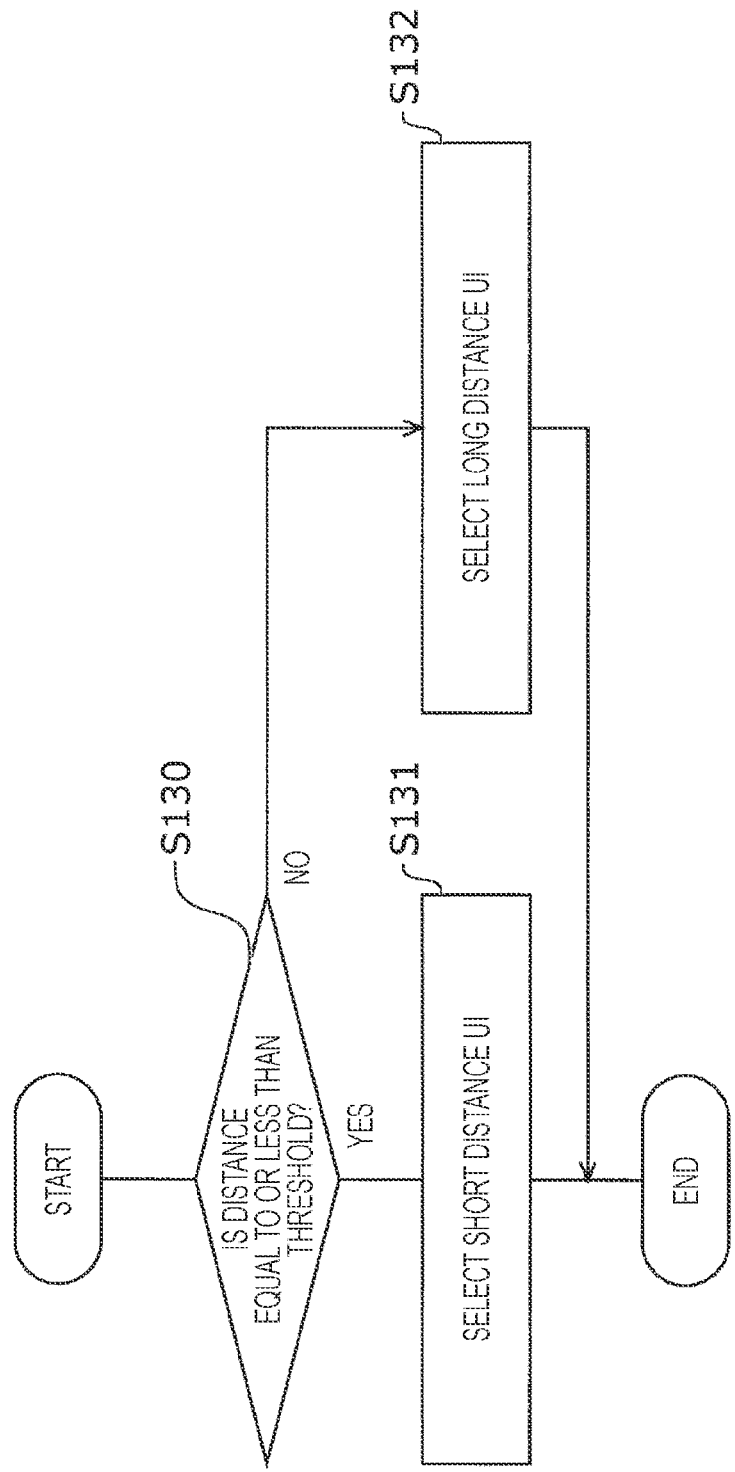
FIG. 11 is a flowchart illustrating part of the processing according to the embodiment.

FIG. 11 is a flowchart illustrating UI display selection processing.

The UI selection unit 106 determines whether or not the distance d estimated in S12 is equal to or less than a threshold (S130). Note that, although comparison with the distance d is used, the distance z described above may be used. In this case, the threshold is only required to be doubled.

In a case where the distance d is equal to or less than the threshold (S130: YES), the UI selection unit 106 selects the short distance UI and stores this result (S131). On the other hand, in a case where the distance d is greater than the threshold (S130: NO), the UI selection unit 106 selects the long distance UI and stores this result (S132). The storage may be performed in the memory 16. In this manner, the UI selection unit 106 switches the UI to be displayed according to a positional relationship between the user P and the mirror M.

Returning to FIG. 8, after the display selection (S13) is performed or in a case where the face cannot be detected (S11: NO), the eye detection unit 122 executes pupil/iris detection processing in the second image (S14). In a case where it is determined as NO in S11, the processing proceeds to S14. It is because there is a possibility that the face cannot be detected by the first camera 10 but the eye can be detected by the second camera 12. For example, it is conceivable that a place other than the face such as a hand of the user P and the like covers most of the face and the face cannot be detected.

Figure 12:
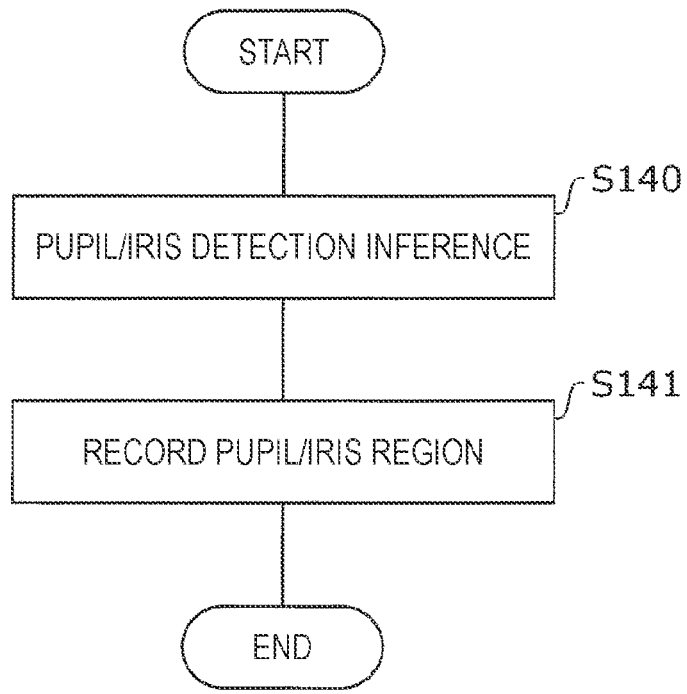
FIG. 12 is a flowchart illustrating part of the processing according to the embodiment.

FIG. 12 is a flowchart illustrating a subroutine of the pupil/iris detection processing (S14). The eye detection unit 122 executes detection inference of the pupil and the iris by using, for example, a learned neural network model (S140).

This model is optimized by performing machine learning in advance using, for example, a large amount of data each with a rectangular label of an image of an eye including a pupil and an iris as training data. Parameters of the optimized model are stored in, for example, the memory 16, and the eye detection unit 122 forms a model and realizes inference by loading hyperparameters and parameters related to the model. For example, a detection result may be indicated by a circle, or may be a region of a face that can be extracted by a curve.

Furthermore, such a model is not limited to be used, and for example, processing of detecting a circular shape by Hough transform and the like may be used. The inference may be further performed using the neural network model after the Hough transform is executed. Furthermore, the Hough transform or the neural network model may be used after a contour is extracted by snake processing and the like. It is not limited thereto, and processing that can extract a circular shape may be used as preprocessing to be input to the neural network model. Furthermore, for example, two circles having different sizes whose centers substantially coincide with each other may be extracted as a pupil and an iris without using the neural network model.

Next, the eye detection unit 122 records a region of the detected pupil and iris (S141). The recording is executed, for example, by storing data in the memory 16. It is not necessary to detect both the pupil and the iris, and processing of detecting only the pupil or only the iris may be performed according to the application.

Returning to FIG. 8, the processor 18 determines whether or not sizes of the detected pupil and iris are appropriate (S15). In a case where the sizes of the pupil and the iris are appropriate (S15: YES), the determination unit 124 executes analysis and determination processing (S16).

Figure 13:
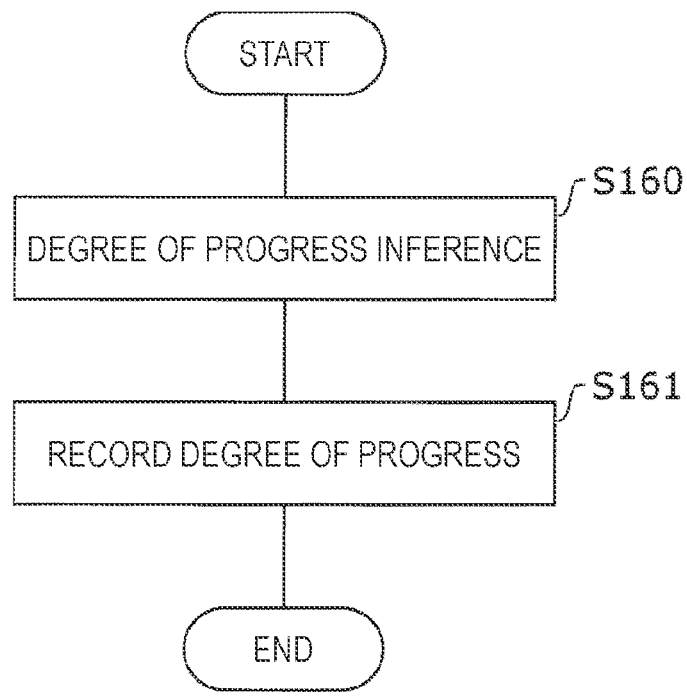
FIG. 13 is a flowchart illustrating part of the processing according to the embodiment.

FIG. 13 is a flowchart illustrating a subroutine of the analysis/determination processing (S16). For example, the determination unit 124 determines whether or not there is an abnormality in the pupil and the iris using the learned neural network model, and furthermore, determines degree of progress in a case where there is a disease (S160).

This model is optimized by performing machine learning in advance using, for example, a large amount of data in which an image of the eye and a value representing the degree of progress of the disease are associated as training data. Parameters of the optimized model are stored in, for example, the memory 16, and the determination unit 124 loads obtained hyperparameters and parameters related to this model, thereby forming a model and realizing inference.

Furthermore, this training data may be acquired by various methods. For example, data in a state of being hit by a flash or data of an infrared camera may be used. On the basis of data that can be acquired by the second camera 12, training using various data may be executed. In this case, a plurality of models may be optimized using each type of training data, and the determination unit 124 may execute inference by changing the model on the basis of data that can be acquired by the second camera 12 or an imaging situation (for example, a situation where the flash has been turned on, infrared rays have been received, and the like) at timing when the second image has been acquired. Furthermore, a plurality of second images may be used in one determination.

Next, the determination unit 124 records the determined degree of progress (S161). The recording is executed, for example, by storing data in the memory 16. As described above, the degree of progress may be represented by a numerical value, and in this case, the determination unit 124 stores this numerical value in the memory 16 as the degree of progress.

Note that at this timing, the processor 18 may store the image of the pupil/iris of the user P acquired by the second camera 12 in the memory.

Returning to FIG. 8, the output unit 140 outputs various states (S17).

Figure 14:
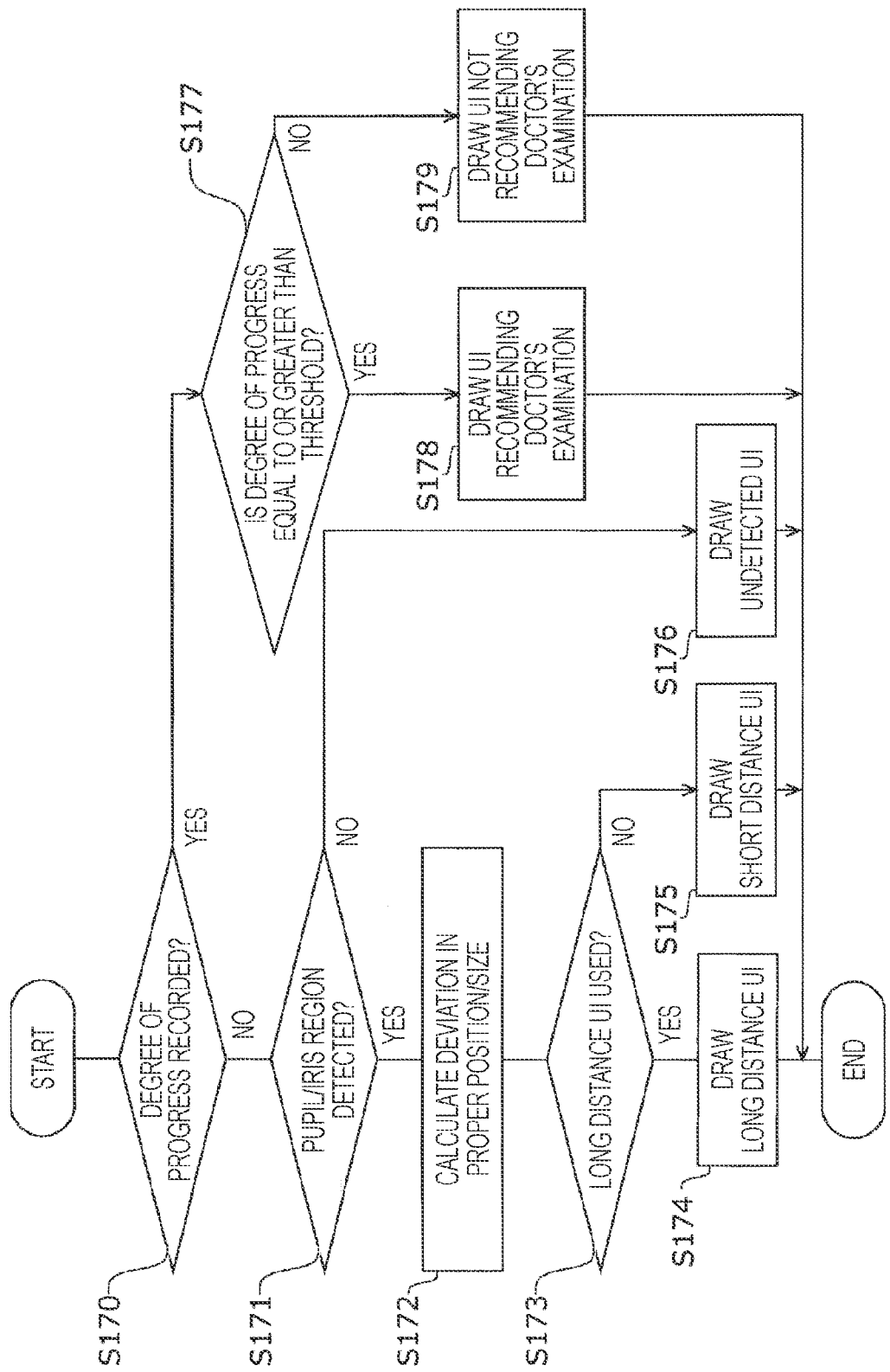
FIG. 14 is a flowchart illustrating part of the processing according to the embodiment.

FIG. 14 is a flowchart illustrating a subroutine of output processing (S17) of the output unit 140. The output unit 140 first determines whether or not there is an estimation result of the degree of progress (S170). Since the estimation result of the degree of progress is stored in the memory 16, for example, the output unit 140 makes this determination by referring to the memory 16.

In a case where there is no estimation result of the degree of progress (S170: NO), it is determined whether or not the pupil/iris region is detected (S171). Since the detection result of the pupil/iris region is stored in the memory 16, for example, the output unit 140 performs this determination by referring to the memory 16.

In a case where the pupil/iris region is detected (S171: YES), the output unit 140 calculates deviation in a proper position and size (S172). In this processing, how much the pupil/iris deviates from an appropriate position for acquiring an image for performing analysis, and how much the pupil/iris deviates from a size suitable for performing analysis are calculated. For example, as illustrated in the right diagram of FIG. 5, for example, the output unit 140 displays the navigation N in a position and size suitable for performing analysis on the display 142. The output unit 140 calculates how much the position and size of the navigation N deviate from the region of the pupil/iris.

The position and size are determined by the performance of the second camera 12, and may be acquired and set at the time of installation or execution similarly to the parameters such as the horizontal angle of view and the like of the first camera 10 described above. The output unit 140 may store these pieces of deviation information in the memory 16.

Next, the output unit 140 determines whether or not the UI selection unit 106 has selected the long distance UI (S173). This determination is executed on the basis of the information recorded in the memory 16 by the UI selection unit 106.

In a case where the long distance UI is selected (S173: YES), the output unit 140 outputs the second image to the display 142 using, for example, the long distance UI as illustrated in FIG. 5 (S174). On the other hand, in a case where the short distance UI is selected (S173: NO), the output unit 140 outputs the second image to the display 142 using, for example, the short distance UI as illustrated in FIG. 6 (S175). The user P adjusts the imaging position of the eye, that is, the position of the terminal device 1 while viewing the second image displayed on the display 142 using the long distance UI or the short distance UI reflected by the mirror M.

In a case where it is determined that the pupil/iris region is not detected in S171 (S171: NO), the output unit 140 outputs that the pupil or the iris is not detected to the display 142 (S176). For example, the image currently acquired by the second camera 12 is directly displayed on the display 142, and the user P is requested to align the eye position. As another example, "pupil and iris not detected" may be displayed in mirror writing on the display 142, and the writing may be output so that it can be read by the user P through the mirror M.

In a case where it is determined in S170 that there is an estimation result of the degree of progress (S170: YES), the output unit 140 determines whether or not the degree of progress acquired from the memory 16 is equal to or greater than a threshold (S177).

In a case where the degree of progress is equal to or greater than the threshold (S177: YES), a UI recommending a doctor's examination is drawn (S178). For example, by displaying a sentence that urges the doctor's examination, recommendation of the examination is transmitted to the user P. As another example, a nearby hospital may be displayed or the user P may be guided to a reservation form by, for example, position information of the terminal device 1, area information set in advance by the user, and the like. Furthermore, the output unit 140 may display a UI that prompts transmission of the image to a doctor on the basis of determination by the user P. The user P can contact a hospital, make a reservation via the Internet and the like, or transmit an image of his/her eye to a doctor on the basis of these drawing results. At the time of transmission, the terminal device 1 may reacquire an image to be transmitted using the various UIs described above in order to acquire a more precise image. Furthermore, an aspect may be employed in which an image can be automatically transmitted to a doctor by opt-in and the like.

In a case where the degree of progression is less than the threshold (S177: NO), a drawing indicating that the doctor's examination is not recommended may be performed (S179). In this manner, the output unit 140 determines whether it is better to receive the doctor's examination from the determination result in the determination unit 124 and performs output to the user P.

After the output of S178 or S179 is completed, the output unit 140 may store a completion flag of simple determination in the memory 16.

Returning to FIG. 8, in a case where the output by the output unit 140 is completed (S18: YES), the terminal device 1 ends the processing. In a case where the processing is not completed (S18: NO), the processing from S10 is repeated.

Note that the processing from S10 to S13 may be performed less frequently than the processing from S14 to S18. In a case where the processing is performed in this manner, the processor 18 may execute, for example, the processing from S10 to S13 after repeating the processing from S14 to S18 a plurality of times.

As described above, according to the present embodiment, in the simple determination of the eye by the user, it is possible to perform the processing in which the position adjustment is simple using the terminal device 1 and the mirror M. Furthermore, by changing the UI displayed on the display 142 according to the distance between the user P and the mirror M, it is possible to display the index so that the position adjustment of the terminal device 1 can be easily understood at any distance within an appropriate range for making determination.

Since this determination processing is in a closed state in the terminal device 1, a user who worries about privacy information can also perform simple determination. On the contrary, in setting of automatically transmitting the image, it is possible to save the trouble of the user P.

In addition, in a case where the determination processing is omitted and the detection can be performed with the appropriate sizes in S15, the image of the second camera 12 may be acquired, the acquired image may be transmitted to a server, and the determination processing may be executed in the server. As another example, the acquired image may be transmitted to a doctor, and the doctor may make a determination by viewing the image.

(Modification 1)

In the embodiment described above, for example, degree of cloudiness of a crystalline lens and the like is determined by acquiring the pupil and the iris of the eye, but it is not limited thereto. For example, a flash may be turned on, or an infrared transmitter and an infrared sensor may be used to implement a simple determination of the inside of the crystalline lens.

(Modification 2)

Not only the pupil and the iris but also the entire eye may be set as a determination target, and the determination may be executed by imaging the entire eye. The processor 18 may determine, for example, various abnormalities related to the eye such as conjunctivitis and the like on the basis of the image of the entire eye.

(Modification 3)

Moreover, other portions of the face may be determined instead of the eye. For example, a target that is difficult for a person to see by himself/herself, and furthermore, is difficult to acquire an image even using a so-called in-camera, such as skin, an oral cavity (throat, tongue, tooth, and the like), and the like, can be acquired similarly to the present embodiment.

(Modification 4)

Figure 15:
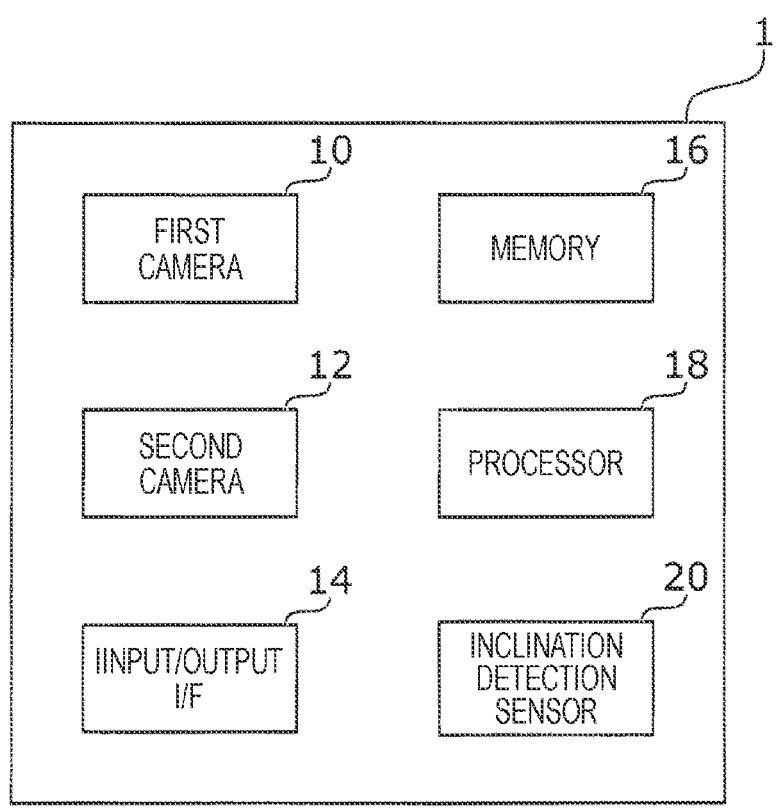
FIG. 15 is a diagram schematically illustrating the terminal device according to an embodiment.

FIG. 15 is a block diagram illustrating a configuration of the terminal device 1 according to a modification. Moreover, the terminal device 1 may include an inclination detection sensor 20.

The inclination detection sensor 20 includes, for example, a plurality of acceleration sensors and gyro sensors. The inclination detection sensor 20 may detect inclination of the terminal device 1 and execute the various calculations described above, for example, the calculation as illustrated in FIG. 14.

Figure 16:
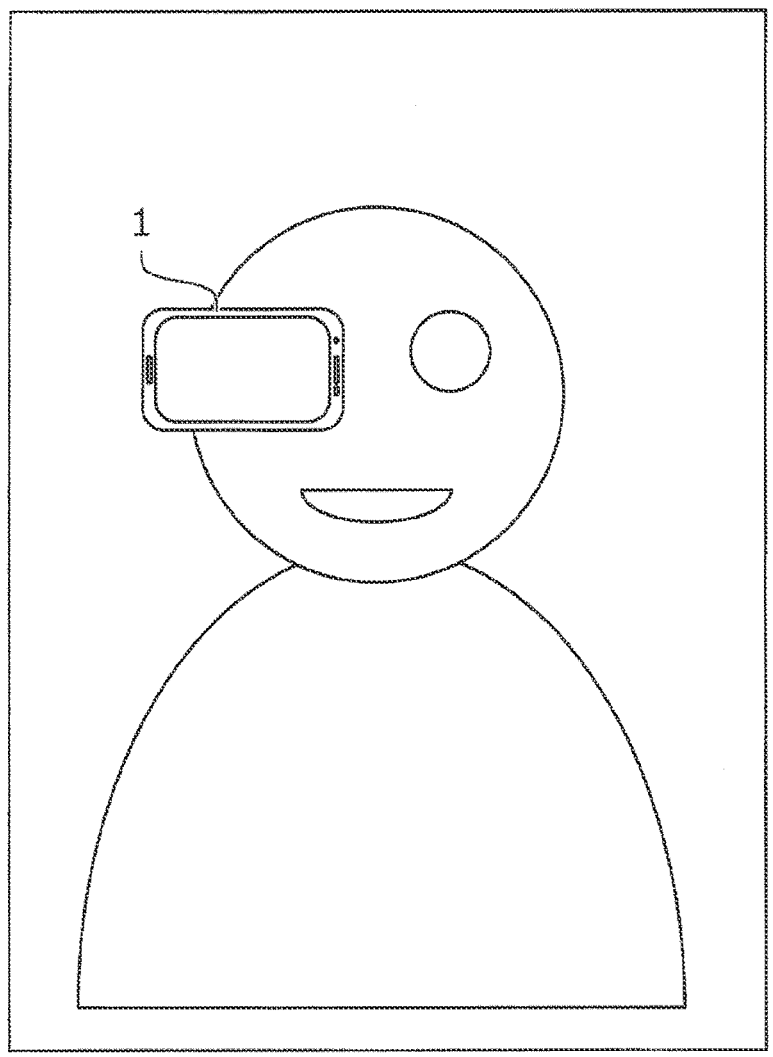
FIG. 16 is a diagram schematically illustrating a usage example of the terminal device according to the embodiment.

For example, in a case where a housing of the terminal device 1 is large, the user P can see the display 142 through the mirror M with respect to one eye, but it may be difficult to see the mirror M through the terminal device 1 with respect to another eye. In such a case, as illustrated in FIG. 16, the terminal device 1 may be inclined by 90 degrees. Even when inclined in this manner, the inclination detection sensor 20 detects the inclination, and thus, it is possible to output navigation for acquiring an appropriate second image of the eye to the user P similarly to the embodiment described above.

Note that even without the inclination detection sensor 20, it is possible to cope with the case as illustrated in FIG. 16. For example, in a case where the face detection unit 102 detects a face, the inclination of the terminal device 1 can be acquired from a vertical direction of the face in the first image.

(Modification 5)

Although only the movement in the horizontal direction with respect to the surface of the display 142 of the terminal device 1 has been focused in the above description, movement in the normal direction, that is, a distance between the terminal device 1 and the face of the user may be drawn so as to be adjusted by the user P.

Figure 17:
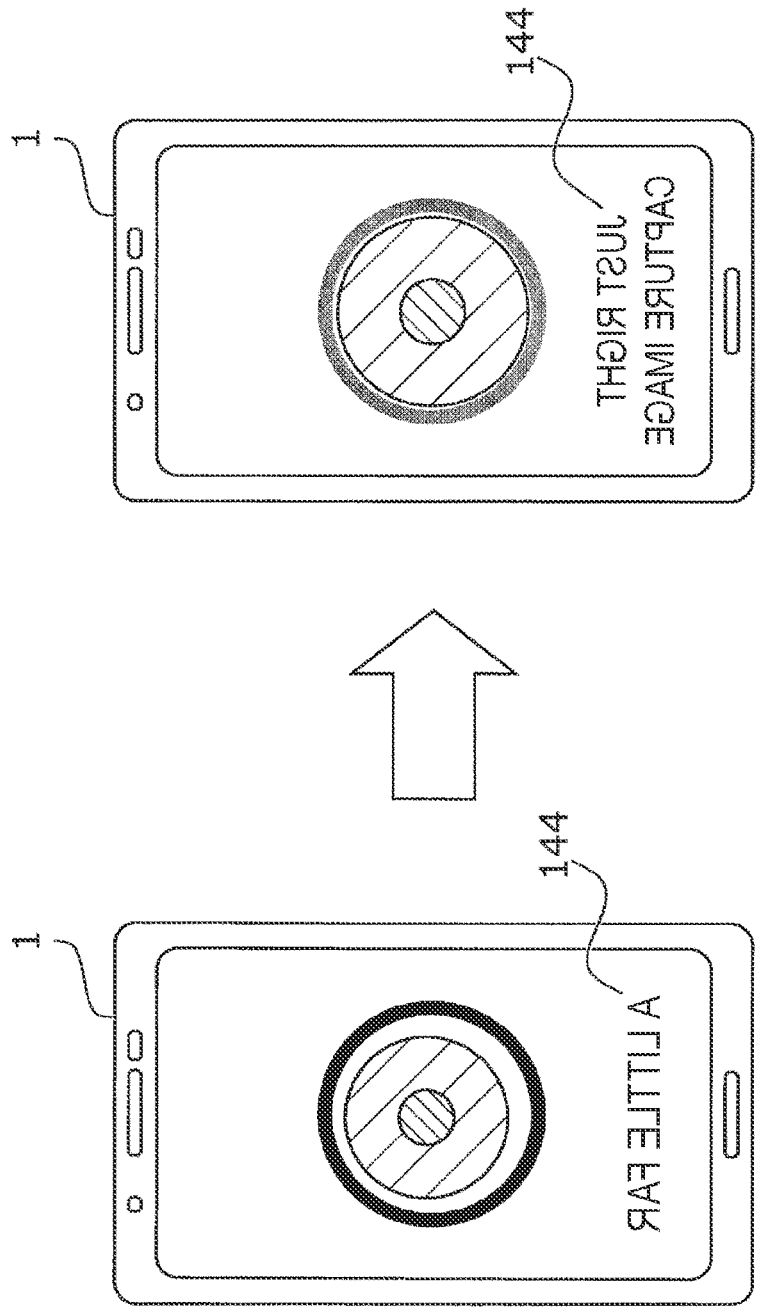
FIG. 17 is a diagram illustrating a display example of the display according to an embodiment.

FIG. 17 is an example of display prompting the user P to adjust a distance between the terminal device 1, more precisely, the second camera 12 and the eye of the user.

For example, the output unit 140 displays such a UI in a case where the sizes of the pupil and the iris are not appropriate in S172 in FIG. 14. For example, in a case where the size of the iris is smaller than the appropriate size, character display such as "a little far" may be displayed to the user. In this case, by displaying the characters as mirror writing, the user P can easily perform reading through the mirror M. Conversely, in a case where the size of the iris is larger than the appropriate size, display such as "slightly close" may be performed. In addition, a direct instruction such as "move closer to face" or "move away from face" may be displayed to cause the user to adjust a position of the terminal device 1 more specifically.

In a case where the position and the size have become appropriate, a message to image may be displayed as illustrated in a right drawing. By performing such display, for example, the user P can be urged not to blink for a while.

The user P may be notified of this indicator such as "close", "far", and "just right" by changing a color of a ring of the navigation N, for example, in addition to the characters. As another example, the user P may be notified by sound from a speaker or vibration by vibration. Various methods for outputting color, sound, and vibration can be considered.

For example, in a case where the notification is made by the color, a red ring may be displayed in a case of being unsuitable, and a green ring may be displayed as it becomes more suitable.

For example, in a case where the notification is made by the sound, the user P may be directly instructed by voice. As another example, continuous or intermittent sounds of low or high pitch may be emitted to notify a far, near, or just right state.

For example, in a case where the notification is made by the vibration, the notification may be made such that the vibration becomes larger or a sense of the vibration becomes shorter as it becomes less suitable.

These examples are given as examples, and operation of the output unit 140 is not limited to these examples.

In a case where the distance between the face of the user P and the terminal device 1 is adjusted in this manner, the distance between the user P and the face may be measured using the second image acquired by the second camera 12. For example, the distance may be measured by using a distance measurement sensor provided together with the second camera 12. As another example, the distance may be measured on the basis of the size of the region of the iris in the second image and performance of the second camera 12 (for example, values corresponding to the angle of view θ and W with respect to the first camera 10 in the example described above). Since the size of the human iris is about 11 to 12 mm in diameter, the distance between the face of the user P, more specifically, the eye and the terminal device 1 can be measured by using this value and, for example, the detection region of the iris by the eye detection unit 122.

(Modification 6)

Figure 18:
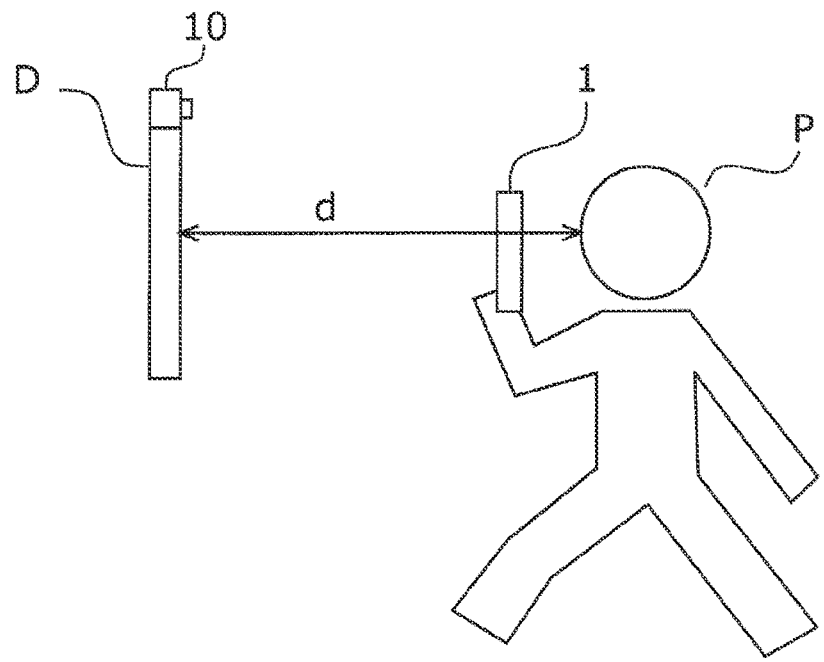
FIG. 18 is a diagram schematically illustrating a usage example of the terminal device according to an embodiment.

FIG. 18 is a diagram illustrating a usage example of the terminal device 1 according to a modification. The terminal device 1 may be used together with a display D instead of the mirror M. For example, the first camera 10 is provided in the display D. Then, the display D displays an image of the user P and the terminal device 1 acquired by the first camera 10.

Even in such a case, operation similar to that of the embodiment and each modification mentioned above can be performed. The display D and the first camera 10 may be provided in, for example, a laptop computer. In this case, the terminal device 1 and the laptop computer can realize the operation similar to that of the embodiment described above by transmitting and receiving data.

Instead of performing all the processing by the terminal device 1, the processing described above may be appropriately distributed between the terminal device 1 and the laptop computer.

Furthermore, a monitor which is not in a state attached to the computer may be used. In this case, the terminal device 1, the display D, and the first camera 10 are connected by a wired or wireless path, and data displayed on the display D and data used for processing in the terminal device 1 are appropriately transmitted.

Figure 19:
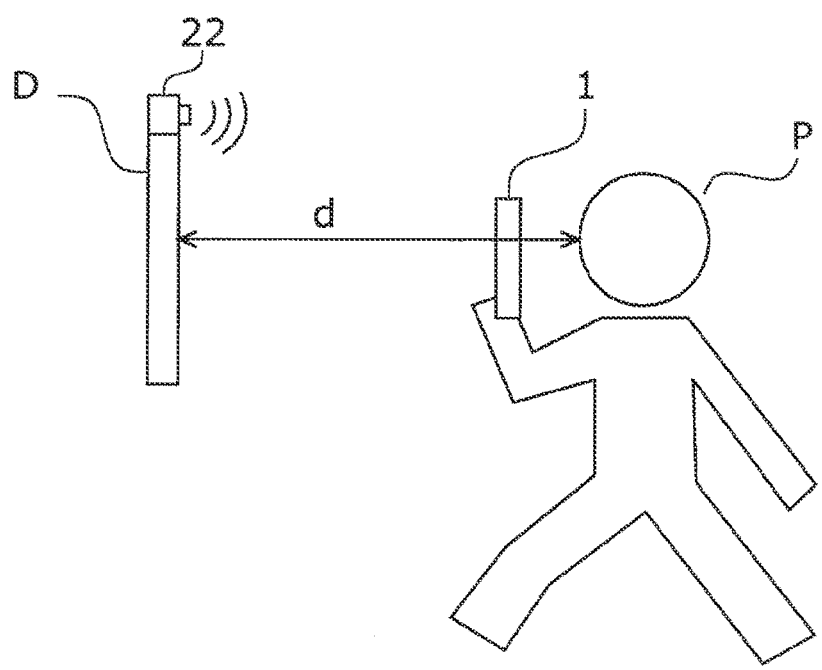
FIG. 19 is a diagram schematically illustrating a usage example of the terminal device according to the embodiment.

FIG. 19 illustrates still another example of such a configuration, and a distance measurement sensor 22 is provided instead of the first camera 10. The distance measurement sensor 22 is, for example, a TOF sensor. By using such a distance measurement sensor 22, there is a possibility that a more accurate distance can be measured than in a case where image processing is performed. Therefore, instead of the first camera 10, the distance measurement sensor 22 may be provided together with the display D. The terminal device 1 may determine a UI on the basis of distance information measured by the distance measurement sensor 22 and display the UI on the display D.

Figure 20:
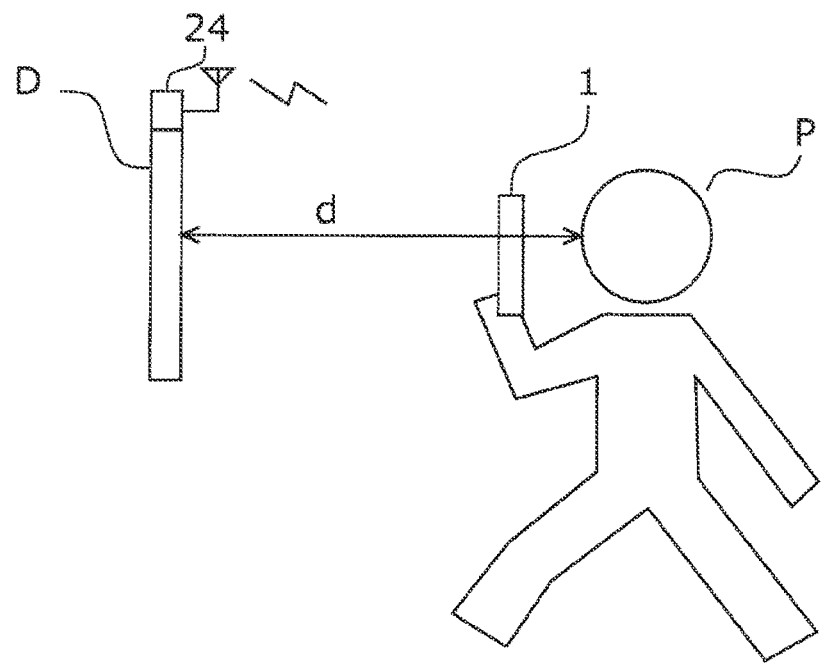
FIG. 20 is a diagram schematically illustrating a usage example of the terminal device according to the embodiment.

FIG. 20 is still another example, and a wireless communication device is provided instead of the first camera 10. For example, according to Wi-Fi and the like, a distance to the terminal device 1 can be estimated according to a radio wave condition. By appropriately transmitting and receiving radio waves, the distance between the terminal device 1 and the display D may be estimated from Wi-Fi parameters and the like, and the UI determined on the basis of this distance information may be drawn on the display D. That is, the distance may be estimated on the basis of a communication state between the wireless device on the display D side and the input/output I/F 14 of the terminal device 1. Furthermore, information acquired by a global positioning system (GPS) and the like may be used.

Note that this method may be applied to a case where the mirror M is used instead of the display D. That is, the distance may be estimated on the basis of a communication state between the wireless device near the mirror M and the terminal device 1.

(Modification 7)

Figure 21:
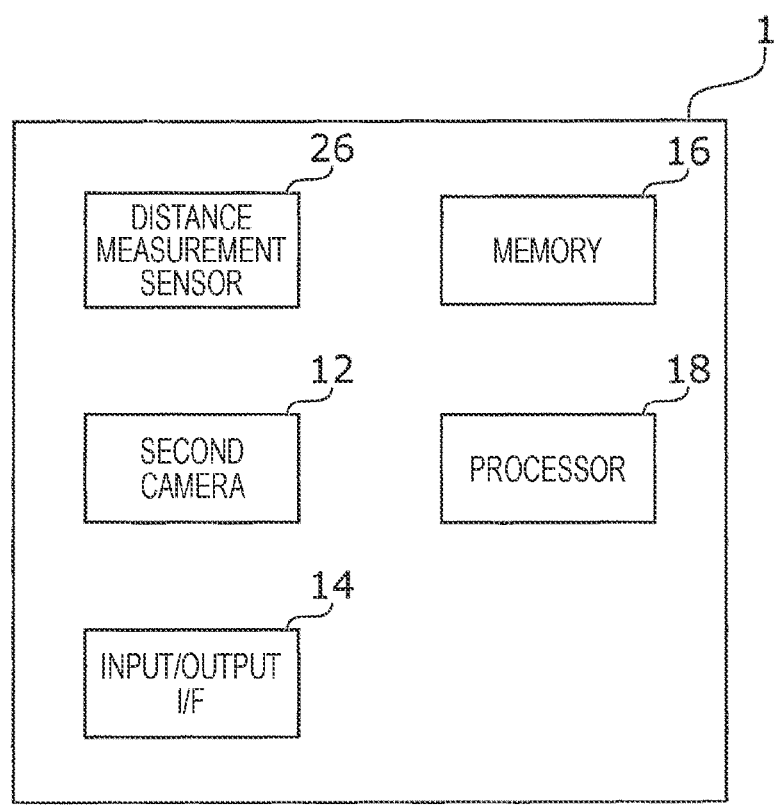
FIG. 21 is a diagram schematically illustrating the terminal device according to an embodiment.

In the modification described above, the distance measurement sensor is provided on the display D side, but the present invention is not limited thereto. For example, as shown in FIG. 21, the terminal device 1 may include a distance measurement sensor 26, and this may be used instead of the first camera.

In this case, the distance measurement sensor 26 measures a distance from the terminal device 1 to the mirror M. The terminal device 1 may determine a UI on the basis of this distance. Moreover, as another example, a distance between the user P and the terminal device 1 may be acquired by the above-described method, and a distance between the user P and the mirror M may be estimated on the basis of the distance between the user P and the terminal device 1 and the distance between the terminal device 1 and the mirror M, and applied to each aspect described above.

(Modification 8)

In all of the above, in the terminal device 1, for example, the display 142 occupies a large region of a side surface thereof. There is no particular problem as long as the display 142 is a simple display device. However, in a case where the display 142 is a touch screen, the user P may touch the display 142 during position adjustment and determination, which may cause, for example, a problem such as minimizing and terminating an application. In order to cope with such a problem, for example, while the user P performs position adjustment, operations such as tapping, flicking, swiping, pinching, and the like may be disabled. Moreover, in this case, only a predetermined region may be set as the effective region, and these operations may be controlled to be switched to be effective on an entire screen by tapping the predetermined region and the like.

(Modification 9)

In all of the above, the long distance UI and the long distance UI are switched using the predetermined distance as the threshold, but this predetermined distance can also be adjusted. For example, by inputting eyesight of the user P in advance, the predetermined distance can be set on the basis of the eyesight of the user P. For example, in a case of a user with good eyesight (hyperopia), the threshold for switching to the short distance UI may be lowered, and conversely, in a case of a user with poor eyesight (myopia), the threshold for switching to the long distance UI may be raised.

Moreover, a Landolt ring and the like may be displayed on the display 142 as accurately as possible on the basis of the distance and the performance of the display 142, and a simple visual acuity test may be performed. This test may be performed, for example, by a method in which the user touches regions on upper, lower, left, and right sides of the Landolt ring of the display 142 to respond a direction, or may be instructed by swiping and the like. A threshold for UI switching based on this result may be set.

(Modification 10)

The user is not specified in the above description, but a function of specifying the user may be provided. For example, the user may be specified by the user inputting an ID. For the specified user, for example, a log can be stored, managed, or browsed, and degree of progress can be determined on the basis of the log. Furthermore, a UI may be changed for every user. For example, switching of the UI may be executed on the basis of eyesight of the user input in advance.

(Modification 11)

In all the aspects described above, the determination of a part of the face, for example, the eye is performed, but an application example is not limited thereto. For example, the terminal device 1 can realize alignment of personal authentication using an iris by executing similar operation. On the basis of an authentication result, the terminal device 1 may be activated, a specific application may be activated, or the authentication result may be transmitted via the Internet.

Furthermore, in combination with the above-described modification 10, the processor 18 may acquire a parameter and the like regarding an application for determination from the personal authentication result by the iris.

Aspects of the present disclosure may be implemented by a program. The program may be stored in a storage unit (the memory 16), and information processing by software may be specifically implemented by hardware. Software processing may be implemented by an analog circuit or a digital circuit, for example, a field programmable gate array (FPGA), an application specific integrated circuit (ASIC), or a digital signal processor (DSP), in addition to a computer.

The embodiments described above may have the following forms.

(1)

A program that causes a processor to execute:

detection of a first target in a first image acquired by a first camera;

estimation of a length of a path from the detected first camera to the first target; and switching of display of a second image acquired by a second camera on the basis of the length of the path, and synthesis of an index for adjusting a position of a second target in the second image.

(2)

The program according to (1), in which the first target is a face of a user, and the second target is an eye of the user.

(3)

The program according to (2), in which the processor processes the first image and the second image acquired by a terminal device, the terminal device including a display, the first camera, and the second camera, the first camera being provided on the same surface as a display surface of the display, and the second camera being provided on a surface opposite to the display surface of the display.

(4)

The program according to (3), in which the processor is caused to execute estimation of a region of the face reflected by a mirror acquired from the first camera, estimation of at least one of a distance from the mirror to the face or a distance from the mirror to the terminal device on the basis of the region of the face, and switching of the display of the second image between a case where the distance is shorter than a predetermined distance and a case where the distance is equal to or longer than the predetermined distance.

(5)

The program according to (1) or (2), in which the processor is caused to execute estimation of a distance from a terminal device including the second camera to a display existing outside the terminal device on the basis of the first image acquired by the first camera included in the display without reflection, and switching of the display of the second image between a case where the distance is shorter than a predetermined distance and a case where the distance is equal to or longer than the predetermined distance.

(6)
The program according to any one of (3) to (5),
in which the processor is caused to execute
generation of the index such that at least a part of the eye falls within a predetermined range.
(7)
The program according to (6),
in which the processor is caused to execute
generation of the index such that at least a pupil of the eye falls within the predetermined range.
(8)
The program according to (7),
in which the processor is caused to execute
generation of the index such that at least an iris of the eye falls within the predetermined range.
(9)
The program according to either one of (6) and (7),
in which the processor is caused to execute
analysis of the interior of the eye.
(10)
The program according to any one of (6) to (9),
in which the processor is caused to execute transmission of an image of the interior of the eye.
(11)
The program according to (8),
in which the processor is caused to execute
performance of authentication based on the iris.
(12)
The program according to any one of (3) to (11),
in which the processor is caused to execute
displaying of the second image and the index on the display.
(13)
The program according to (1),
in which the first target is a face of a user, and
the second target is facial skin or an oral cavity of the user.
(14)
An information processing apparatus including:
a processor,
in which the processor
estimates a distance from a display to a user on the basis of a first image of the user and a terminal device captured by a first camera that captures an image in the same direction as a display surface of the display, and
switches a second image captured by a second camera included in the terminal device on the basis of the distance, and outputs an image synthesized with an index to the display.
(15)
A terminal device including:
a display;
a first camera that captures an image in the same direction as a display surface of the display;
a second camera that captures an image in a direction opposite to the display surface of the display; and
a processor,
in which the processor
estimates either one of a distance from a mirror to a face of a user and a distance from the mirror to the terminal device on the basis of a first image captured by the first camera of the face and the terminal device reflected by the mirror, and
switches a second image captured by the second camera on the basis of the distance, and outputs an image synthesized with an index to the display.
(16)
The program, the information processing apparatus, or the terminal device according to any one of (1) to (15),
in which the processor
determines whether the second camera is at an appropriate position on the basis of the index, and
generates the index based on a determination result.
(17)
The program, the information processing apparatus, or the terminal device according to (16),
in which the processor
assigns information including mirror writing to the index.
(18)
The program, the information processing apparatus, or the terminal device according to (16) or (17),
in which the processor
assigns color information to the index.
(19)
The program, the information processing apparatus, or the terminal device according to any one of (1) to (18),
in which the processor
determines whether the second camera is at an appropriate position on the basis of the index, and
outputs sound on the basis of a determination result.
(20)
The program, the information processing apparatus, or the terminal device according to any one of (1) to (16),
in which the processor
determines whether the second camera is at an appropriate position on the basis of the index, and
outputs vibration on the basis of a determination result.
(21)
The program, the information processing apparatus, or the terminal device according to any one of (1) to (20),
in which the processor
estimates the distance on the basis of an output from a TOF sensor.
(22)
The information processing apparatus according (14),
in which the processor
estimates the distance by a communication state between the terminal device and the display.
(23)
The program, the information processing apparatus, or the terminal device according to any one of (2) to (22),
in which the processor
switches the second image on the basis of eyesight of the user.
(24)
A server including a second processor that executes at least part of processing in the processor of (1) to (23).
(25)
A non-transitory computer readable medium that records a program for causing the processor according to any one of (1) to (23) to execute processing.

Aspects of the present disclosure are not limited to the above-described embodiments, and include various conceivable modifications. The effects of the present disclosure are not limited to the above-described contents. The components in each embodiment may be appropriately combined and applied. That is, various additions, modifications, and partial deletions can be made without departing from the conceptual idea and gist of the present disclosure derived from the contents defined in the claims and equivalents thereof.

REFERENCE SIGNS LIST

1 Terminal device
10 First camera

12 Second camera
14 Input/output I/F
16 Memory
18 Processor
100 First processing unit
102 Face detection unit
104 Distance estimation unit
106 UI selection unit
120 Second processing unit
122 Eye detection unit
124 Determination unit
140 Output unit
20 Inclination detection sensor
22 Distance measurement sensor
24 Wireless communication device
26 Distance measurement sensor

The invention claimed is:

1. A non-transitory computer-readable medium having stored thereon, computer-executable instructions which, when executed by a processor, cause a computer to execute operations, the operations comprising:
   acquiring, by a first camera, a first image;
   detecting a first target in the acquired first image;
   estimating a length of a path from the first camera to the detected first target, wherein
      the first target is a face of a user;
   acquiring, by a second camera, a second image;
   switching of display of the second image, wherein the display of the second image is switched based on the length of the path; and
   synthesizing an index for adjusting a position of a second target in the second image, wherein
      the second target is an eye of the user.

2. The non-transitory computer-readable medium according to claim 1, the operations further comprising:
   processing the acquired first image and the acquired second image, wherein
      a terminal device includes a display screen, the first camera, and the second camera,
      the first camera is on a first surface that is same as a display surface of the display screen, and
      the second camera is on a second surface opposite to the display surface of the display screen.

3. The non-transitory computer-readable medium according to claim 2, the operations further comprising:
   estimating, based on the acquired first image, a region of the face reflected by a mirror;
   estimating, based on the estimated region of the face, at least one of a first distance from the mirror to the face or a second distance from the mirror to the terminal device, wherein
      the length of the path is one of the first distance or the second distance; and
   switching of the display of the second image between a case where the length of the path is shorter than a specific distance and a case where the length of the path is equal to or longer than the specific distance.

4. The non-transitory computer-readable medium according to claim 1, the operations further comprising:
   estimating a third distance from a terminal device including the second camera to a display screen existing outside the terminal device, based on the first image acquired by the first camera included in the display screen without reflection; and
   switching of the display of the second image between a case where the third distance is shorter than a specific distance and a case where the third distance is equal to or longer than the specific distance.

5. The non-transitory computer-readable medium according to claim 2, the operations further comprising:
   generating of the index such that at least a part of the eye falls within a specific range.

6. The non-transitory computer-readable medium according to claim 5, the operations further comprising:
   generating of the index such that at least a pupil of the eye falls within the specific range.

7. The non-transitory computer-readable medium according to claim 6, the operations further comprising:
   generating of the index such that at least an iris of the eye falls within the specific range.

8. The non-transitory computer-readable medium according to claim 5, the operations further comprising:
   analyzing an interior of the eye.

9. The non-transitory computer-readable medium according to claim 5, the operations further comprising:
   transmitting an image of an interior of the eye.

10. The non-transitory computer-readable medium according to claim 7, the operations further comprising:
    performing authentication based on the iris.

11. The non-transitory computer-readable medium according to claim 2, the operations further comprising:
    displaying of the second image and the index on the display screen.

12. An information processing apparatus, comprising:
    a processor, wherein the processor is configured to:
       estimate a distance from a display screen to a face of a user, based on a first image of the user and a terminal device captured by a first camera, wherein
          the first camera captures the first image in a same direction as a display surface of the display screen; and
       switch a second image based on the distance, wherein
          the second image is captured by a second camera included in the terminal device; and
       output the switched second image synthesized with an index to the display screen, wherein
          a position of a second target in the second image is adjusted based on the index, and
          the second target is an eye of the user.

13. A terminal device, comprising:
    a display;
    a first camera configured to capture a first image in a same direction as a display surface of the display;
    a second camera configured to capture a second image in a direction opposite to the display surface of the display; and
    a processor, wherein the processor is configured to:
       estimate one of a first distance from a mirror to a face of a user or a second distance from the mirror to the terminal device, based on a first image of the face and the terminal device reflected by the mirror, wherein the first image is captured by the first camera; and
       switch the second image captured by the second camera based on one of the first distance or the second distance; and
       output the switched second image synthesized with an index to the display, wherein
          a position of a second target in the second image is adjusted based on the index, and
          the second target is an eye of the user.

* * * * *